(12) United States Patent
Aklivanh et al.

(10) Patent No.: US 12,262,966 B2
(45) Date of Patent: Apr. 1, 2025

(54) METHOD AND CIRCUIT FOR SUPERVISION OF PROTECTIVE-EARTH CONTINUITY IN MEDICAL DEVICES USING A LOCK-IN AMPLIFIER

(71) Applicant: AURIS HEALTH, INC., Redwood City, CA (US)

(72) Inventors: Eyal Aklivanh, Redwood City, CA (US); Jonathan Bernard, Redwood City, CA (US); Chase Paul Hathaway, Redwood City, CA (US); Martin Carnogursky, San Francisco, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 18/902,797

(22) Filed: Sep. 30, 2024

(65) Prior Publication Data

US 2025/0017670 A1    Jan. 16, 2025

Related U.S. Application Data

(63) Continuation of application No. PCT/IB2023/053262, filed on Mar. 31, 2023.

(60) Provisional application No. 63/326,653, filed on Apr. 1, 2022.

(51) Int. Cl.
| | |
|---|---|
| *A61B 34/30* | (2016.01) |
| *A61B 34/00* | (2016.01) |
| *B25J 19/02* | (2006.01) |
| *B25J 19/06* | (2006.01) |
| *G01R 31/52* | (2020.01) |

(52) U.S. Cl.
CPC .............. *A61B 34/30* (2016.02); *A61B 34/25* (2016.02); *B25J 19/02* (2013.01); *B25J 19/06* (2013.01); *G01R 31/52* (2020.01); *A61B 2034/301* (2016.02)

(58) Field of Classification Search
CPC ... A61B 34/30; A61B 34/25; A61B 2034/301; B25J 19/02; B25J 19/06; G01R 31/52
See application file for complete search history.

(56) References Cited

FOREIGN PATENT DOCUMENTS

| | | |
|---|---|---|
| CN | 113400322 A | 9/2021 |
| JP | S58-143738 A | 8/1983 |
| JP | H06-007703 Y2 | 3/1994 |
| JP | H09-327512 A | 12/1997 |
| JP | 2018-079340 A | 5/2018 |

OTHER PUBLICATIONS

International Search Report and Written Opinion dated Sep. 18, 2023 for Application No. PCT/IB2023/053262, 7 pgs.

*Primary Examiner* — Scott Luan

(74) *Attorney, Agent, or Firm* — Frost Brown Todd LLP

(57) ABSTRACT

A robotic system may include an electrical ground line and a protective earth line electrically coupled to the electrical ground line. The robotic system may also include a testing circuit coupled to the protective-earth line via an isolation capacitor. The testing circuit may include a lock-in amplifier and may be configured to measure an impedance for the protective-earth line through the isolation capacitor. Methods for testing or monitoring protective-earth lines are also disclosed herein.

20 Claims, 21 Drawing Sheets

METHOD AND CIRCUIT FOR SUPERVISION OF PROTECTIVE-EARTH CONTINUITY IN MEDICAL DEVICES USING A LOCK-IN AMPLIFIER

PRIORITY

This application is a continuation of International Patent Application No. PCT/IB2023/053262, filed Mar. 31, 2023, which claims priority to U.S. Provisional Patent Application No. 63/326,653, filed Apr. 1, 2022, the disclosures of each of which are incorporated by reference herein, in their entirety.

TECHNICAL FIELD

The systems and methods disclosed herein are directed to systems with protective-earth connections, and more particularly to medical systems having protective-earth connections.

BACKGROUND

A robotically enabled medical system is capable of performing a variety of medical procedures, including both minimally invasive procedures, such as laparoscopy, and non-invasive procedures, such as endoscopy (e.g., bronchoscopy, ureteroscopy, gastroscopy, etc.). Such robotic medical systems may include a metal enclosure and robotic arms configured to control the movement of medical tool(s) during a given medical procedure.

SUMMARY

The systems, methods and devices of this disclosure each have several innovative aspects, no single one of which is solely responsible for the desirable attributes disclosed herein.

Medical devices with metal enclosures require a functional protective-earth (PE) connection to protect patients and operators from receiving an electrical shock. To achieve a functional PE connection, the metal enclosure can be connected to an electrical ground (GND) line.

It can be beneficial to have a means of testing the PE connection(s) during the lifetime of a medical device to detect whether the PE connection(s) have degraded over time, particularly for medical devices having few connections between the metal enclosure and the GND line. However, testing the PE connection(s) during the lifetime of the medial device can be challenging. First, applying a test current to the metal enclosure can pose an electric shock hazard if the test current is not kept to a low level (e.g., less than 100 microamps, or less than 50 microamps). Second, a PE connection between the metal enclosure and the GND line can have a low impedance (e.g., less than 1 ohm) and thus an output of applying the test current can also be low (e.g., less than 100 microvolts) and therefore difficult to detect and measure. Third, the PE connection can be affected by electromagnetic interference which increases noise and makes measurement of small signals more challenging.

In one aspect, a robotic system includes an electrical ground line and a protective-earth line electrically coupled to the electrical ground line at a first point. The robotic system further includes a testing circuit (also sometimes called a monitoring circuit) coupled to the protective-earth line at a second point via an isolation capacitor. the testing circuit includes a lock-in amplifier and configured to measure an impedance for the protective-earth line.

In another aspect, a robotic system includes an electrical ground line, a protective-earth line, and a testing circuit coupled to the protective-earth line via an isolation capacitor and configured to measure an impedance of the electrical ground line to the protective-earth line through the isolation capacitor.

In another aspect, a robotic system includes an electrical ground line, a protective-earth line, and a testing circuit coupled to the protective-earth line and configured to measure an impedance of the electrical ground line to the protective-earth line.

In another aspect, a method for testing a protective-earth line includes applying a test signal through (or to) an isolation capacitor electrically coupled to the protective-earth line and obtaining a signal from the protective-earth line via the isolation capacitor in response to the test signal. The method also includes measuring an impedance for the protective-earth line based on the obtained signal, the measuring performed by a lock-in amplifier; comparing the determined impedance with a baseline impedance; and providing information indicating the outcome of the comparison. In some embodiments, the method is performed by one or more processors executing instructions store in memory.

In yet another aspect, a method for testing a protective-earth line includes providing a test current through an isolation capacitor electrically coupled to the protective-earth line and obtaining a voltage signal through the isolation capacitor in response to the test current. The method also includes determining an impedance for the protective-earth line based on the obtained voltage signal; and providing information indicating continuity of the protective-earth line based on the determined impedance. In some embodiments, the method is performed by one or more processors executing instructions store in memory.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the inventive subject matter.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations.

A. Robotic System-Cart.

Figure 1:
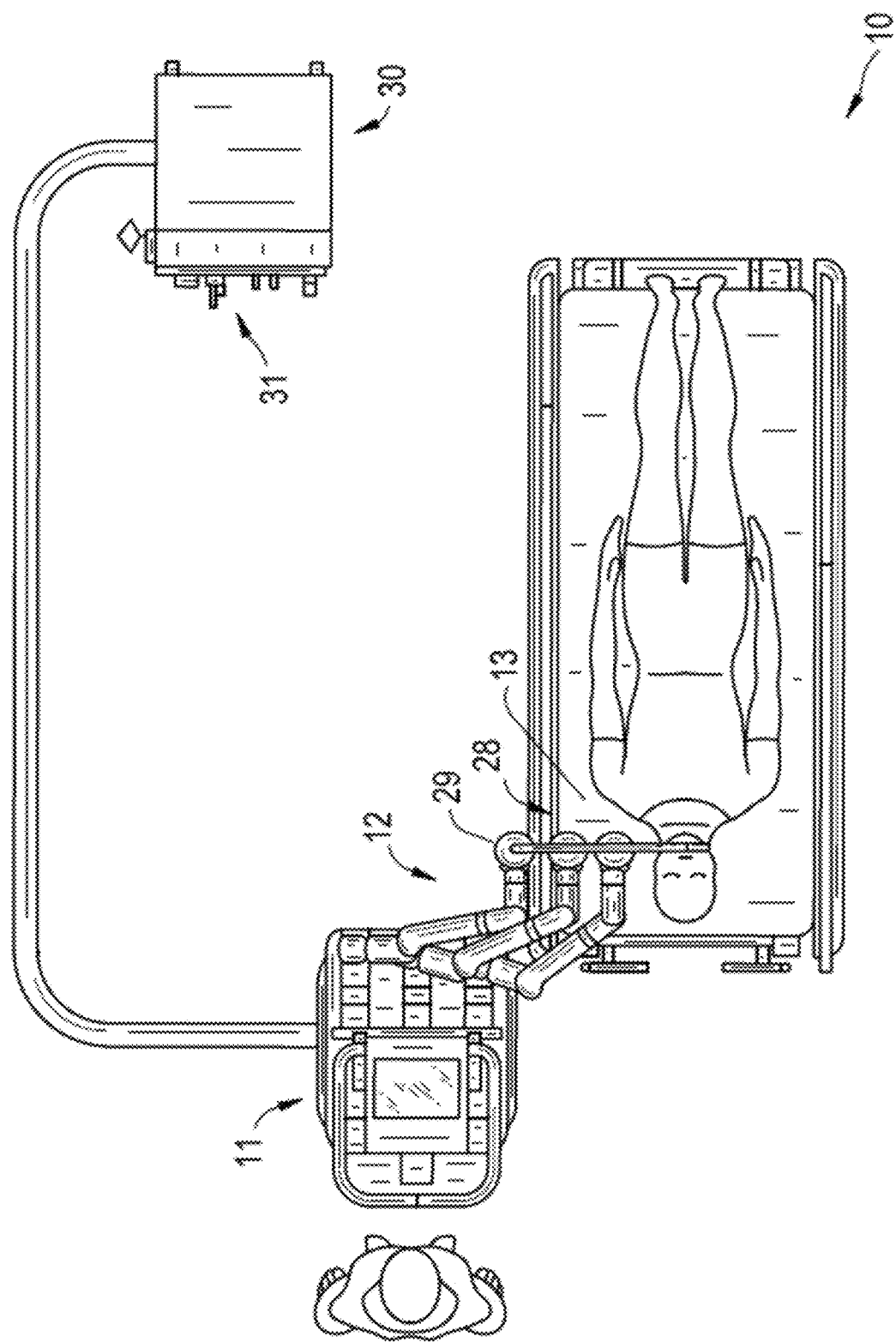
FIG. 1 illustrates an embodiment of a cart-based robotic system arranged for diagnostic and/or therapeutic bronchoscopy procedure(s), according to some embodiments.
Figure 2:
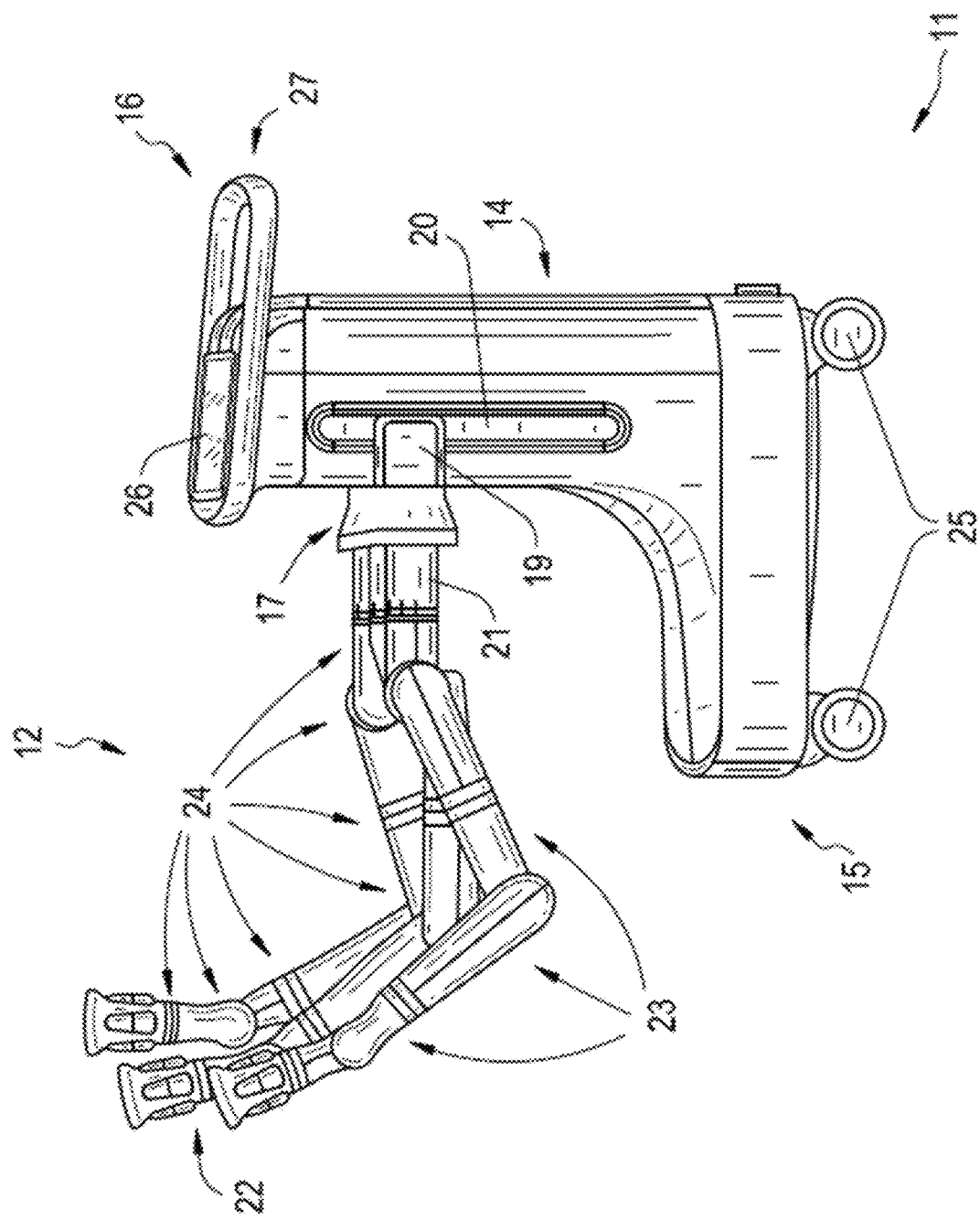
FIG. 2 depicts further aspects of the robotic system of FIG. 1, according to some embodiments.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines (such as in FIGS. 3 and 4), and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 31 is housed in a body that is separate from the tower 30.

FIG. 2 provides a detailed illustration of an embodiment of the cart 11 from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intra-operative data. Potential preoperative data on the touchscreen 26 may include preoperative plans, navigation and mapping data derived from preoperative computerized tomography (CT) scans, and/or notes from preoperative patient interviews. Intra-operative data on display may include optical information provided from the tool, sensor and coordinate information from sensors, as well as vital patient statistics, such as respiration, heart rate, and/or pulse.

Figure 3:
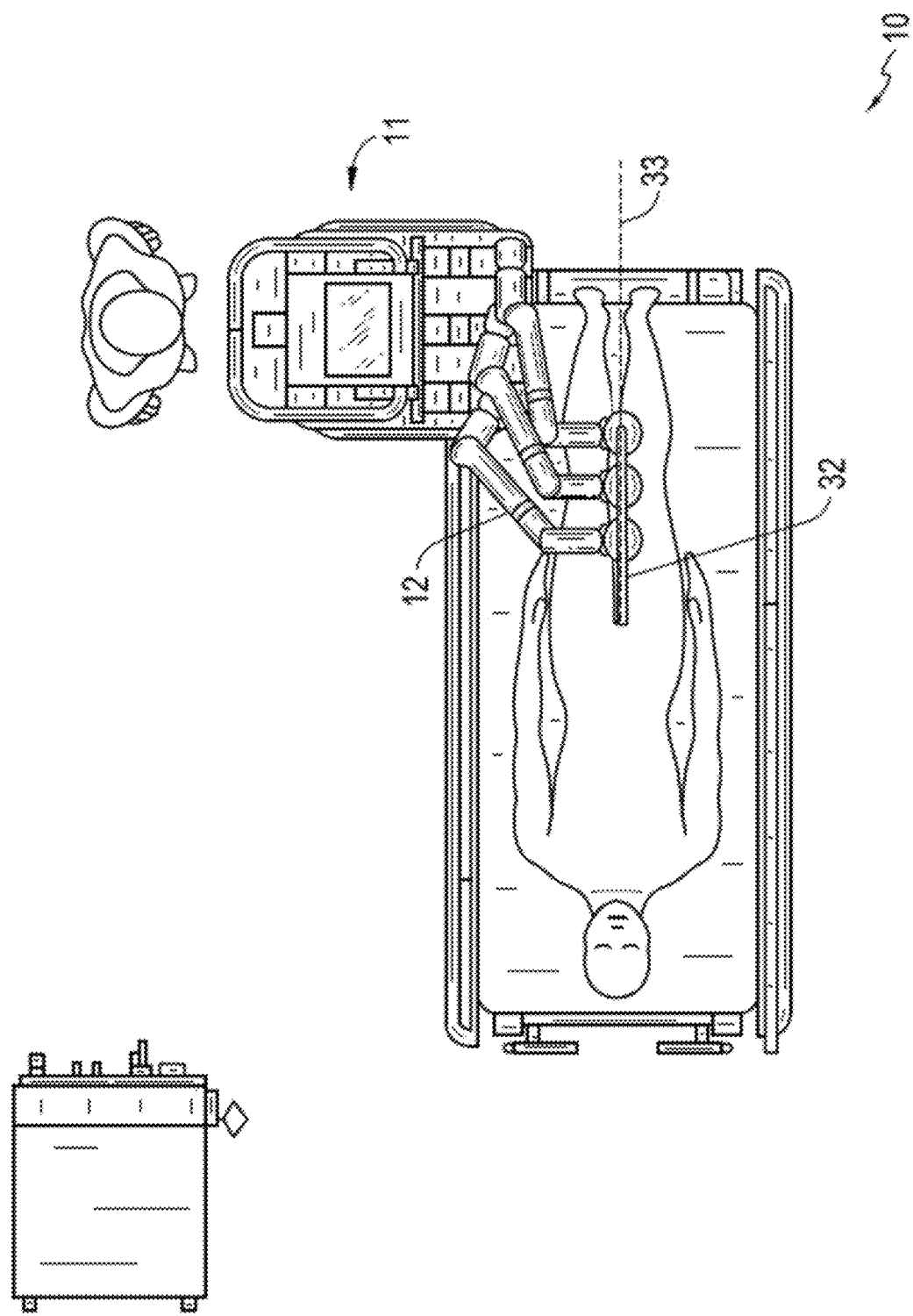
FIG. 3 illustrates an embodiment of the robotic system of FIG. 1 arranged for ureteroscopy, according to some embodiments.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
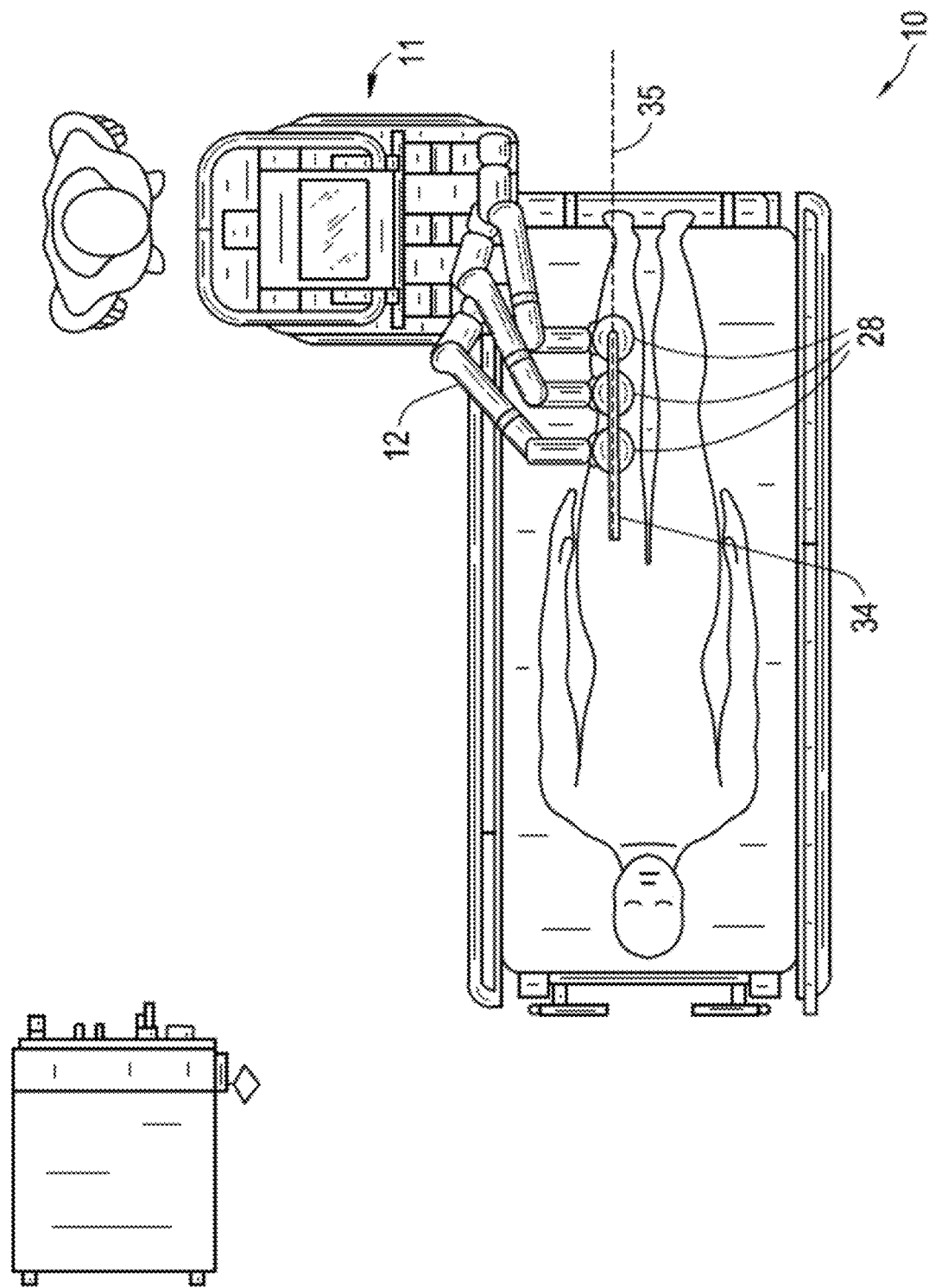
FIG. 4 illustrates an embodiment of the robotic system of FIG. 1 arranged for a vascular procedure, according to some embodiments.

FIG. 4 illustrates an embodiment of a robotically enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System-Table.

Figure 5:
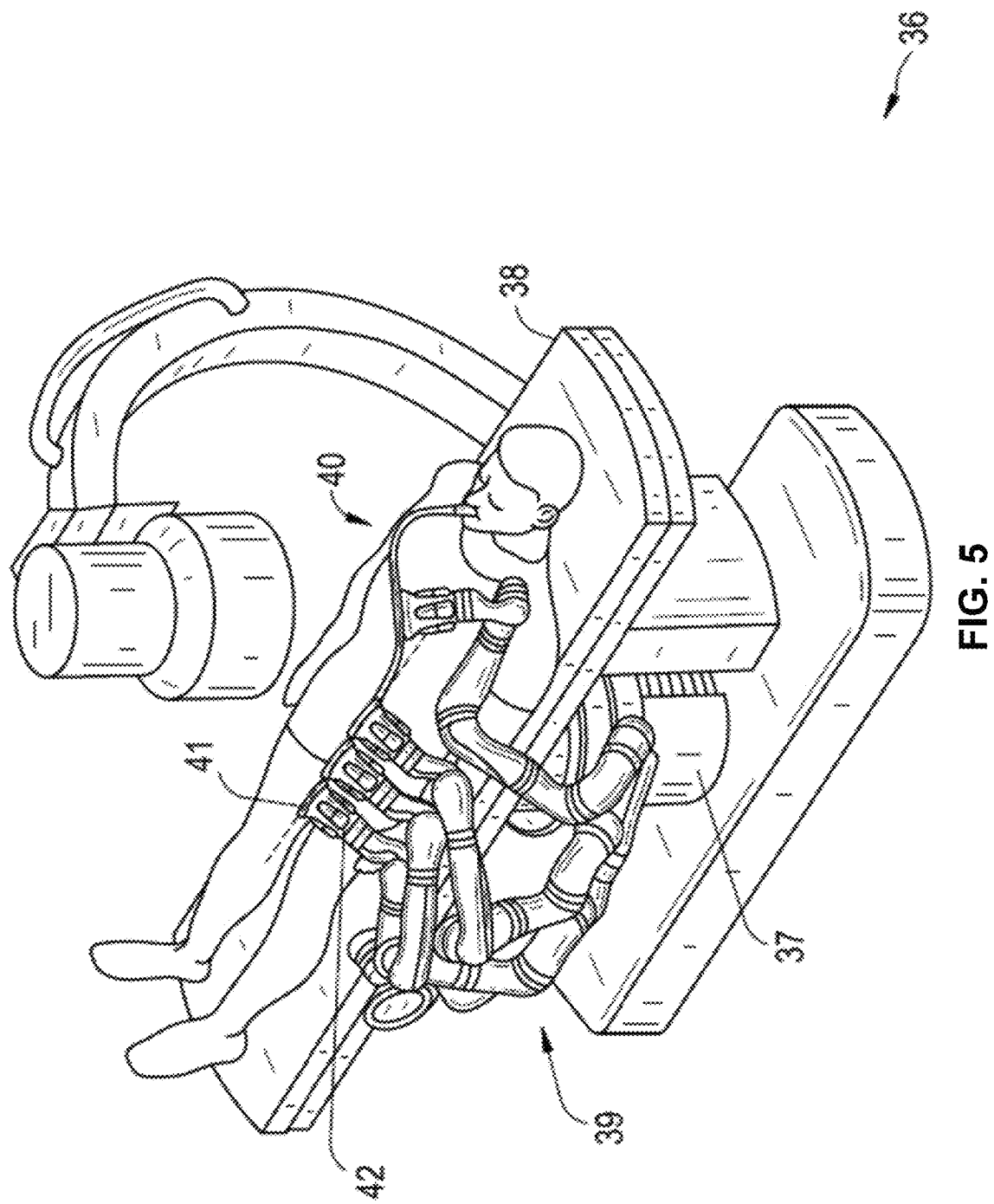
FIG. 5 illustrates an embodiment of a table-based robotic system arranged for a bronchoscopy procedure, according to some embodiments.

Embodiments of the robotically enabled medical system may also incorporate the patient's table. Incorporation of the table may reduce the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient.

The system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 6:
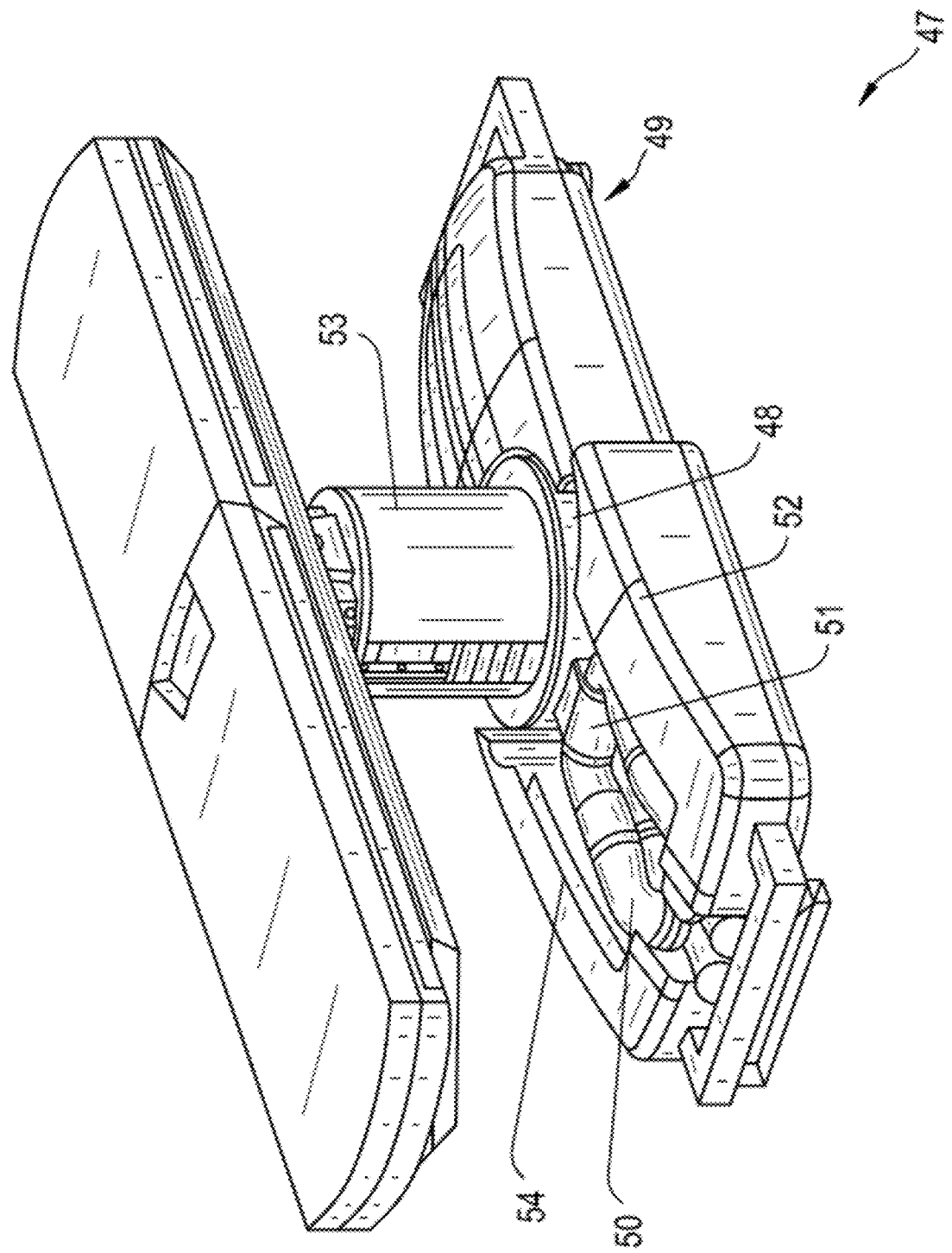
FIG. 6 illustrates an example system configured to stow robotic arm(s), according to some embodiments.

In some embodiments, a table base may stow and store the robotic arms when not in use. FIG. 6 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use.

Figure 7:
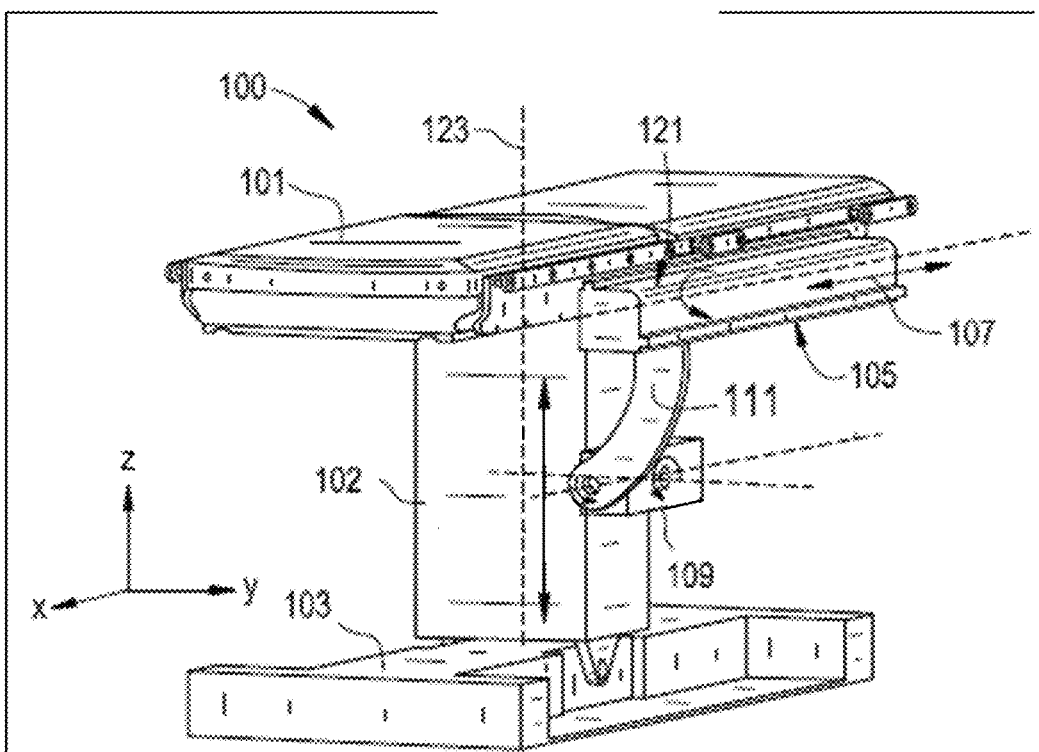
FIG. 7 illustrates an alternative embodiment of a table-based robotic system, according to some embodiments.
Figure 8:
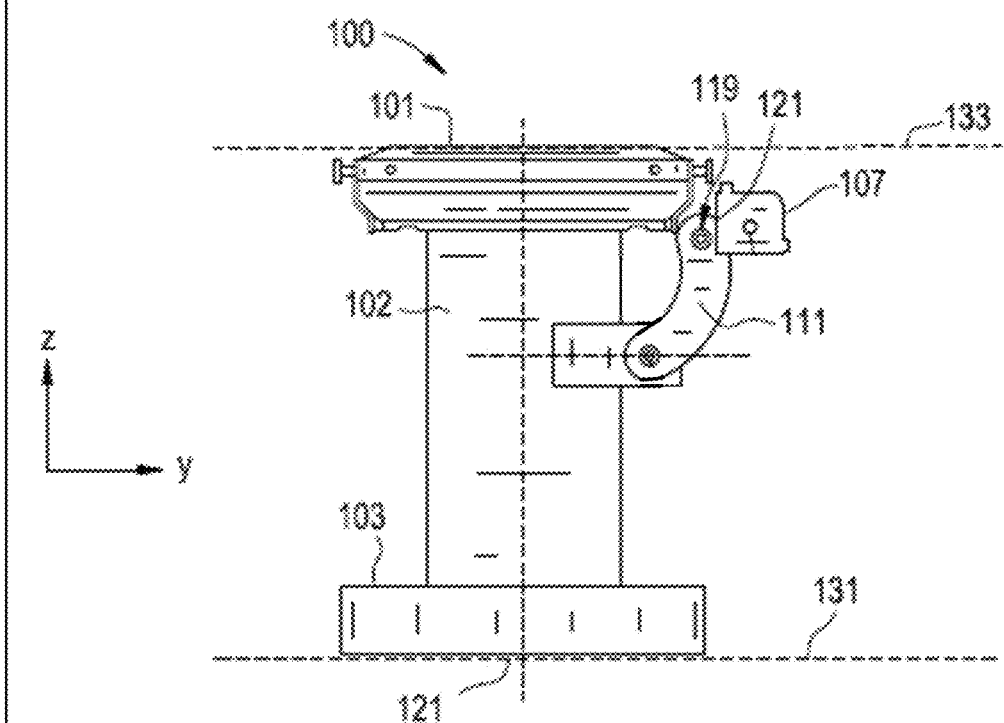
FIG. 8 illustrates an end view of the table-based robotic system of FIG. 7, according to some embodiments.

FIGS. 7 and 8 illustrate isometric and end views of an embodiment of a table-based surgical robotics system 100. The surgical robotics system 100 includes one or more adjustable arm supports 105 that can be configured to support one or more robotic arms (see, for example, FIG. 9) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 7 and 8, the arm support 105 is configured with four degrees of freedom, which are illustrated with arrows in FIG. 7. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 7 and 8 can comprise a table supported by a column 102 that is mounted to a base 103. The base 103 and the column 102 support the table 101 relative to a support surface. A floor axis 131 and a support axis 133 are shown in FIG. 8.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

Figure 9:
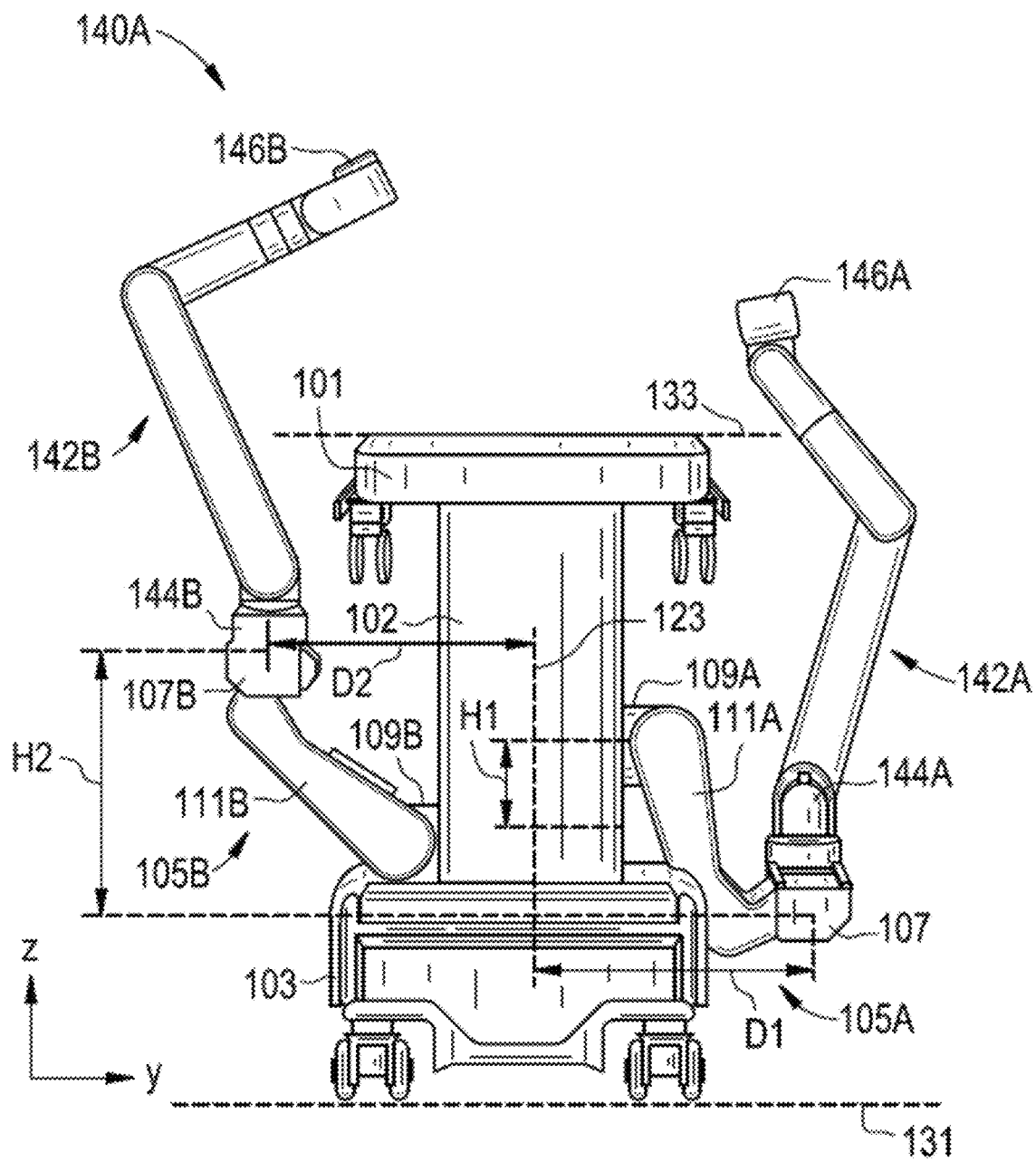
FIG. 9 illustrates an end view of a table-based robotic system with robotic arms attached thereto, according to some embodiments.

FIG. 9 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
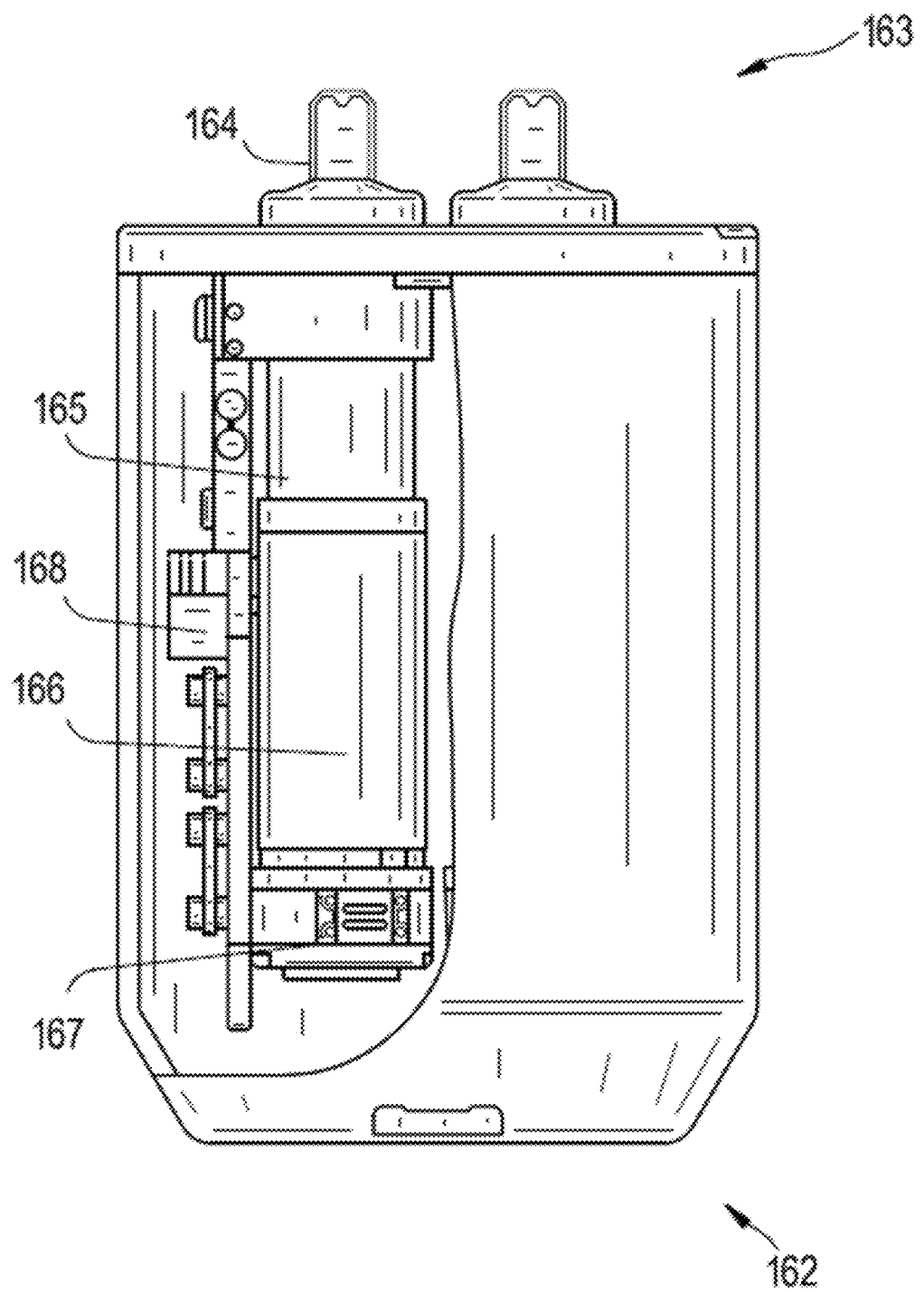
FIG. 10 illustrates an example instrument driver, according to some embodiments.
Figure 11:
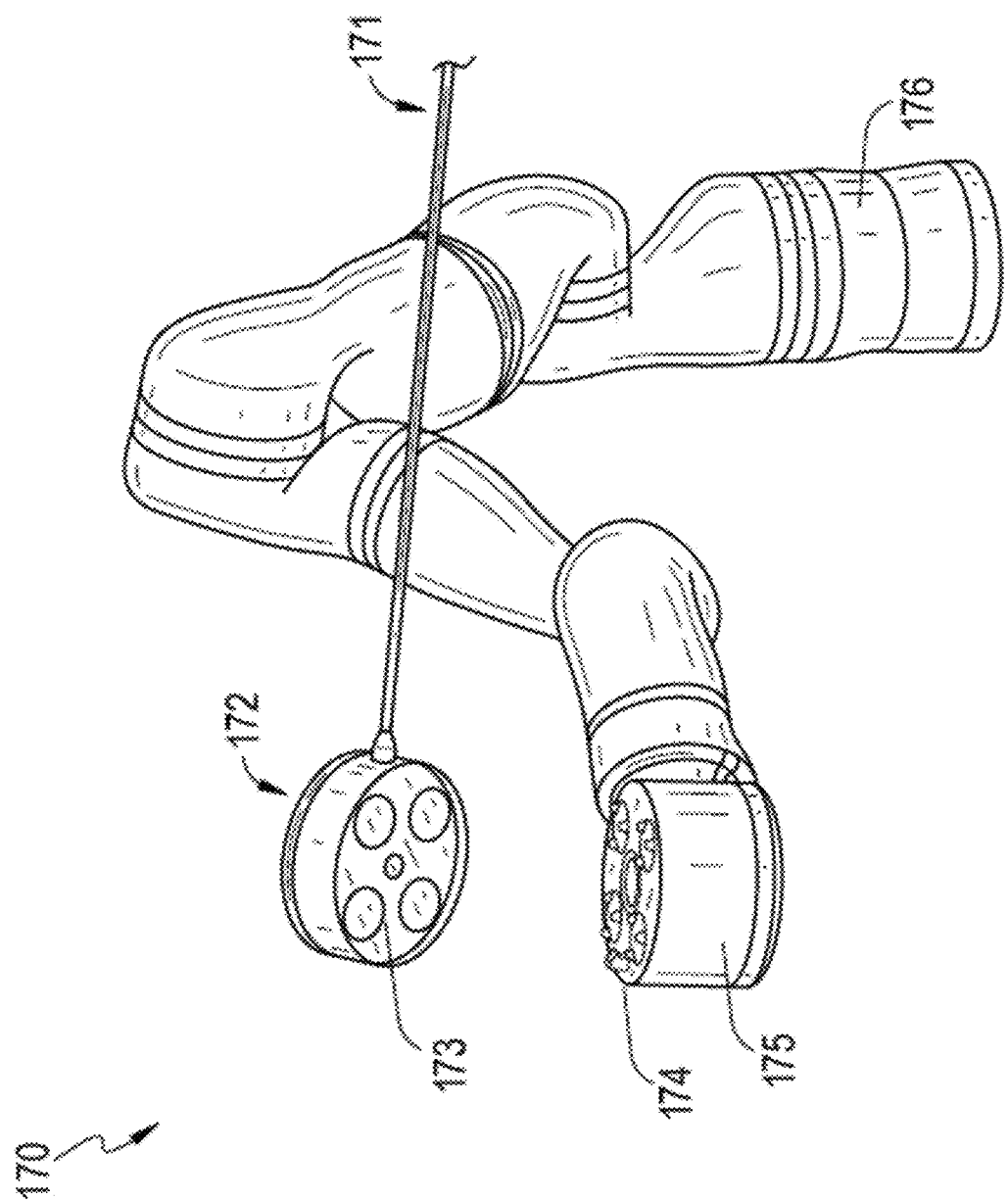
FIG. 11 illustrates an example medical instrument with a paired instrument driver, according to some embodiments.

FIG. 10 illustrates an example instrument driver. Positioned at the distal end of a robotic arm, instrument driver 162 comprises of one or more drive units 163 arranged with parallel axes to provide controlled torque to a medical instrument via drive shafts 164. Each drive unit 163 comprises an individual drive shaft 164 for interacting with the instrument, a gear head 165 for converting the motor shaft rotation to a desired torque, a motor 166 for generating the drive torque, an encoder 167 to measure the speed of the motor shaft and provide feedback to the control circuitry, and control circuitry 168 for receiving control signals and actuating the drive unit. Each drive unit 163 being independent controlled and motorized, the instrument driver 162 may provide multiple (four as shown in FIG. 11) independent drive outputs to the medical instrument. In operation, the control circuitry 168 would receive a control signal, transmit a motor signal to the motor 166, compare the resulting motor speed as measured by the encoder 167 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

FIG. 11 illustrates an example medical instrument with a paired instrument driver. Like other instruments designed for use with a robotic system, medical instrument 170 comprises an elongated shaft 171 (or elongate body) and an instrument base 172. The instrument base 172, also referred to as an "instrument handle" due to its intended design for manual interaction by the physician, may generally comprise rotatable drive inputs 173, e.g., receptacles, pulleys or spools, that are designed to be mated with drive outputs 174 that extend through a drive interface on instrument driver 175 at the distal end of robotic arm 176. When physically connected, latched, and/or coupled, the mated drive inputs 173 of instrument base 172 may share axes of rotation with the drive outputs 174 in the instrument driver 175 to allow the transfer of torque from drive outputs 174 to drive inputs 173. In some embodiments, the drive outputs 174 may comprise splines that are designed to mate with receptacles on the drive inputs 173.

The elongated shaft 171 is designed to be delivered through either an anatomical opening or lumen, e.g., as in endoscopy, or a minimally invasive incision, e.g., as in laparoscopy. The elongated shaft 171 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 174 of the instrument driver 175. When designed for endoscopy, the distal end of a flexible elongated shaft may include a steerable or controllable bending section that may be articulated and bent based on torque received from the drive outputs 174 of the instrument driver 175.

Torque from the instrument driver 175 is transmitted down the elongated shaft 171 using tendons along the shaft 171. These individual tendons, such as pull wires, may be individually anchored to individual drive inputs 173 within the instrument handle 172. From the handle 172, the tendons are directed down one or more pull lumens along the elongated shaft 171 and anchored at the distal portion of the elongated shaft 171, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 173 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 171, where tension from the tendon cause the grasper to close.

In endoscopy, the tendons may be coupled to a bending or articulating section positioned along the elongated shaft 171 (e.g., at the distal end) via adhesive, control ring, or other mechanical fixation. When fixedly attached to the distal end of a bending section, torque exerted on drive inputs 173 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 171 to allow for controlled articulation in the desired bending or articulable sections.

In endoscopy, the elongated shaft 171 houses a number of components to assist with the robotic procedure. The shaft may comprise of a working channel for deploying surgical tools (or medical instruments), irrigation, and/or aspiration to the operative region at the distal end of the shaft 171. The shaft 171 may also accommodate wires and/or optical fibers to transfer signals to/from an optical assembly at the distal tip, which may include of an optical camera. The shaft 171 may also accommodate optical fibers to carry light from proximally located light sources, such as light emitting diodes, to the distal end of the shaft.

At the distal end of the instrument 170, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft.

Figure 12:
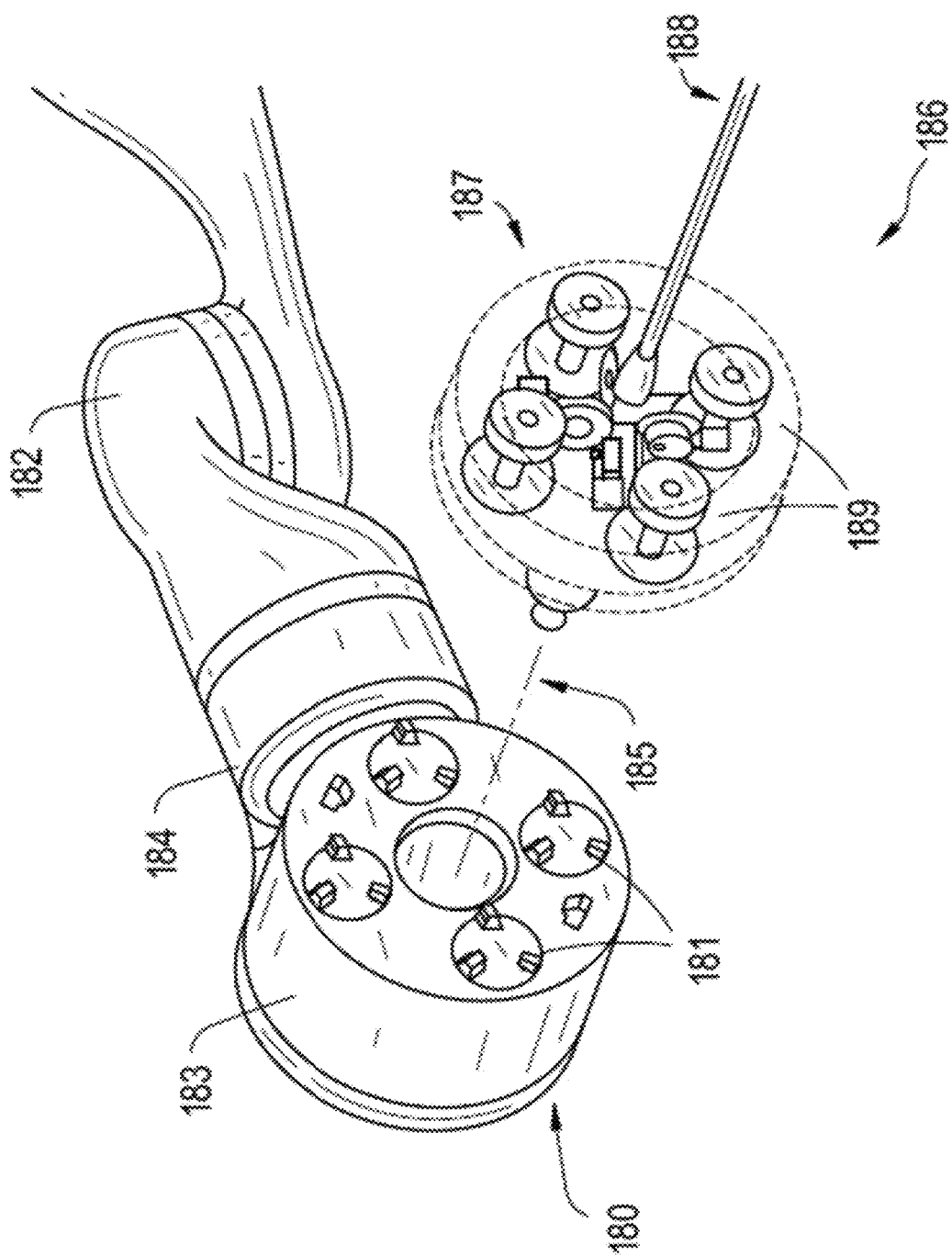
FIG. 12 illustrates an alternative design for an instrument driver and instrument where the axes of the drive units are parallel to the axis of the elongated shaft of the instrument, according to some embodiments.

FIG. 12 illustrates an alternative design for an instrument driver and instrument where the axes of the drive units are parallel to the axis of the elongated shaft of the instrument. As shown, a circular instrument driver 180 comprises four drive units with their drive outputs 181 aligned in parallel at the end of a robotic arm 182. The drive units, and their respective drive outputs 181, are housed in a rotational assembly 183 of the instrument driver 180 that is driven by one of the drive units within the assembly 183. In response to torque provided by the rotational drive unit, the rotational assembly 183 rotates along a circular bearing that connects the rotational assembly 183 to the non-rotational portion 184 of the instrument driver. In other embodiments, the rotational assembly 183 may be responsive to a separate drive unit that is integrated into the non-rotatable portion 184, and thus not in parallel to the other drive units. The rotational mechanism 183 allows the instrument driver 180 to rotate the drive units, and their respective drive outputs 181, as a single unit around an instrument driver axis 185.

Like earlier disclosed embodiments, an instrument 186 may comprise an elongated shaft portion 188 and an instrument base 187 (shown with a transparent external skin for discussion purposes) comprising a plurality of drive inputs 189 (such as receptacles, pulleys, and spools) that are configured to receive the drive outputs 181 in the instrument driver 180. Unlike prior disclosed embodiments, instrument shaft 188 extends from the center of instrument base 187 with an axis substantially parallel to the axes of the drive inputs 189, rather than orthogonal as in the design of FIG. 11.

When coupled to the rotational assembly 183 of the instrument driver 180, the medical instrument 186, comprising instrument base 187 and instrument shaft 188, rotates in combination with the rotational assembly 183 about the instrument driver axis 185. Since the instrument shaft 188 is positioned at the center of instrument base 187, the instrument shaft 188 is coaxial with instrument driver axis 185 when attached. Thus, rotation of the rotational assembly 183 causes the instrument shaft 188 to rotate about its own longitudinal axis.

Figure 13:
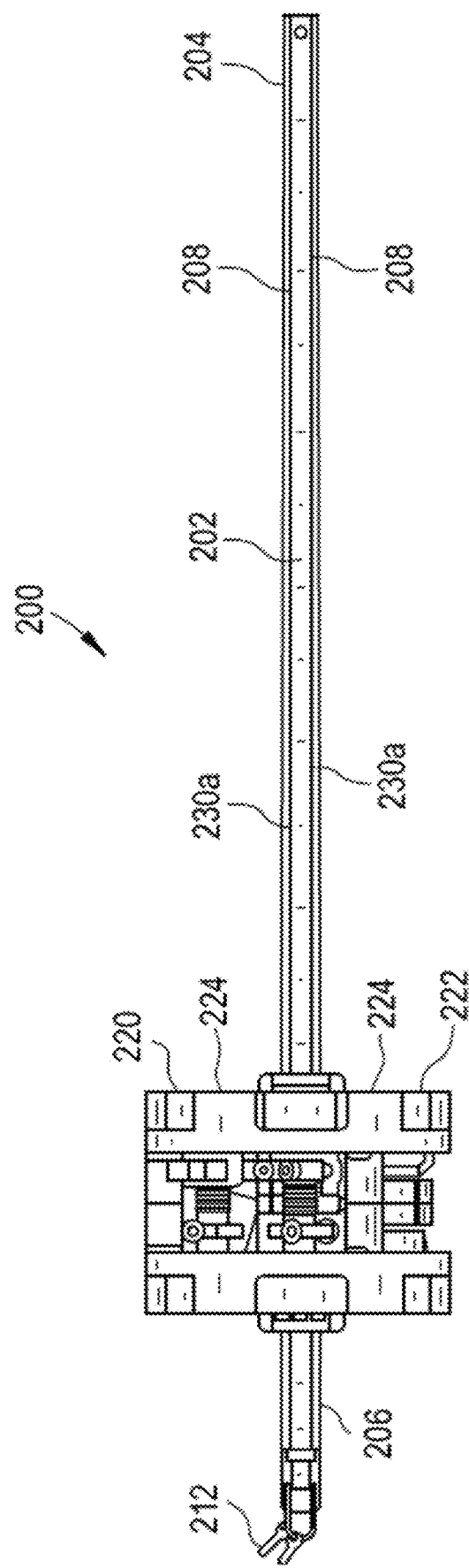
FIG. 13 illustrates an instrument having an instrument-based insertion architecture, according to some embodiments.

FIG. 13 illustrates an instrument having an instrument-based insertion architecture in accordance with some embodiments. The instrument 200 can be coupled to any of the instrument drivers discussed above. The instrument 200 comprises an elongated shaft 202, an end effector 212 connected to the shaft 202, and a handle 220 coupled to the shaft 202. The elongated shaft 202 comprises a tubular member having a proximal portion 204 and a distal portion 206. Manipulation of one or more cables 230a (e.g., via an instrument driver) results in actuation of the end effector 212.

The instrument handle 220, which may also be referred to as an instrument base, may generally comprise an attachment interface 222 having one or more mechanical inputs 224, e.g., receptacles, pulleys or spools, that are designed to be reciprocally mated with one or more torque couplers on an attachment surface of an instrument driver.

In some embodiments, the instrument 200 comprises a series of pulleys or cables that enable the elongated shaft 202 to translate relative to the handle 220. In other words, the instrument 200 itself comprises an instrument-based insertion architecture that accommodates insertion of the instrument, thereby minimizing the reliance on a robot arm to provide insertion of the instrument 200. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
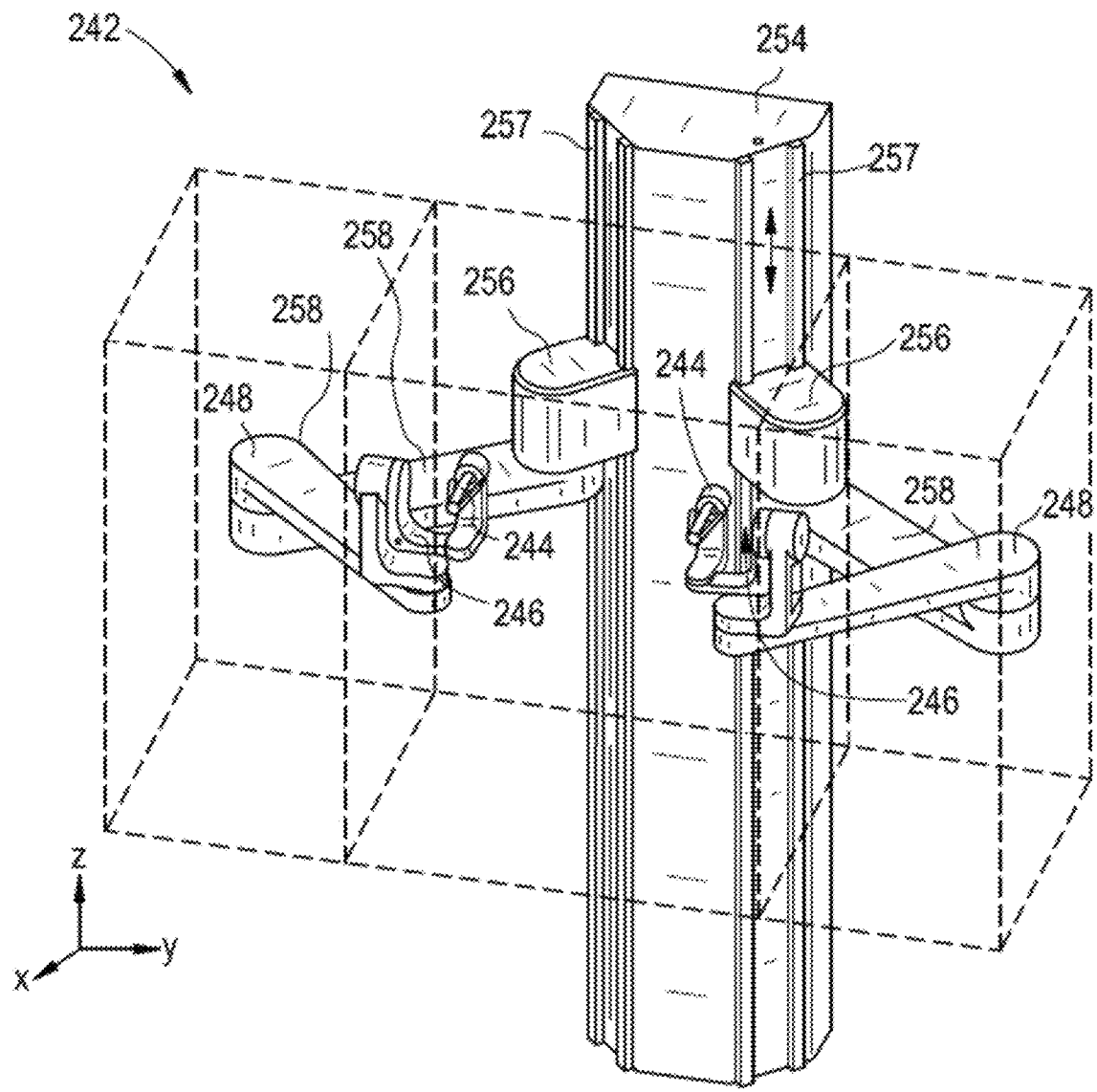
FIG. 14 illustrates an example controller, according to some embodiments.

FIG. 14 is a perspective view of an embodiment of a controller 242. In the illustrated embodiment, the controller 242 is configured to allow manipulation of two medical instruments, and includes two handles 244. Each of the handles 244 is connected to a gimbal 246. Each gimbal 246 is connected to a positioning platform 248.

As shown in FIG. 14, each positioning platform 248 includes a SCARA arm (selective compliance assembly robot arm) 258 coupled to a column 254 by a prismatic joint 256. The prismatic joints 256 are configured to translate along the column 254 (e.g., along rails 257) to allow each of the handles 244 to be translated in the z-direction, providing a first degree of freedom. The SCARA arm 258 is configured to allow motion of the handle 244 in an x-y plane, providing two additional degrees of freedom.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Protective-Earth Systems for Medical Devices.

Embodiments of the disclosure relate to systems and methods for testing and/or monitoring protective-earth connections within medical systems and devices.

Medical systems and devices, such as the systems described above, can include a protective-earth system to ground the enclosures (of such systems and/or devices) for reducing the risk of electric shock to patients and operators. In some embodiments, the protective-earth system includes a protective-earth line. In some embodiments, the electrical ground line includes a return path for power and logic components of the medical system (or device). In some embodiments, the protective-earth line connects the system enclosure to an electrical ground line. In some embodiments, the protective-earth line includes the system enclosure. In some embodiments, the protective-earth system includes a testing circuit coupled to the protective-earth line and configured to measure an impedance through the protective-earth line to the electrical ground line. The measured impedance may be used to monitor or determine the continuity of the protective-earth line.

One skilled in the art will appreciate that the systems and devices described herein can be applied in non-medical contexts as well. For example, the protective-earth system described herein may be implemented in robotic systems and devices used in non-medical environments.

Figure 15A:
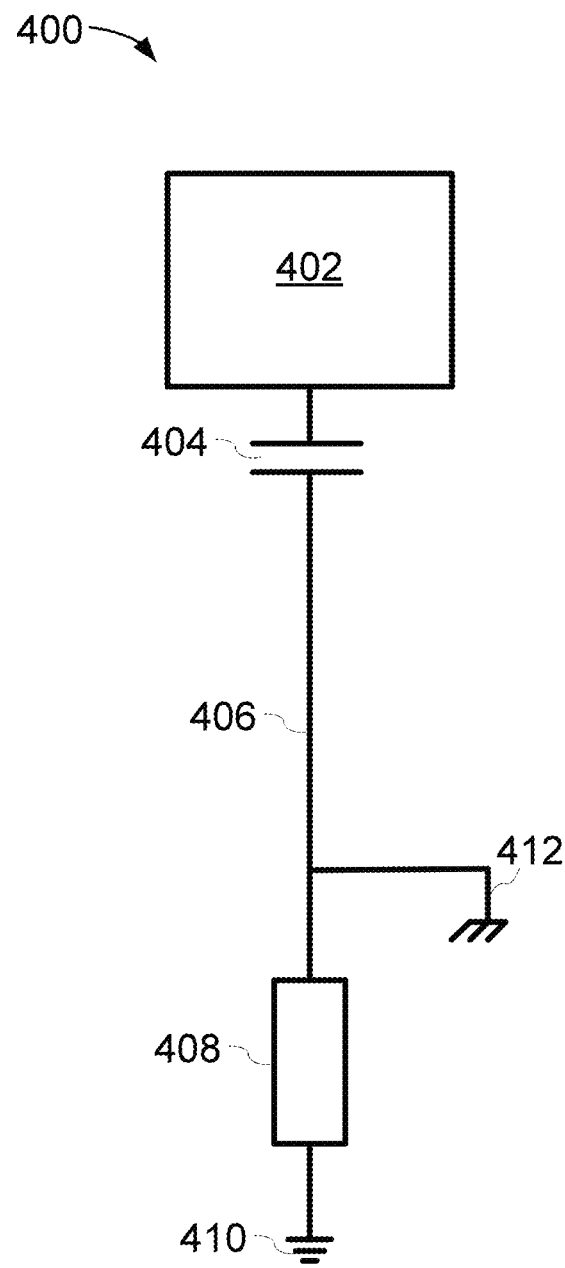
FIGS. 15A-15C illustrate example protective-earth systems, according to some embodiments.
Figure 15C:
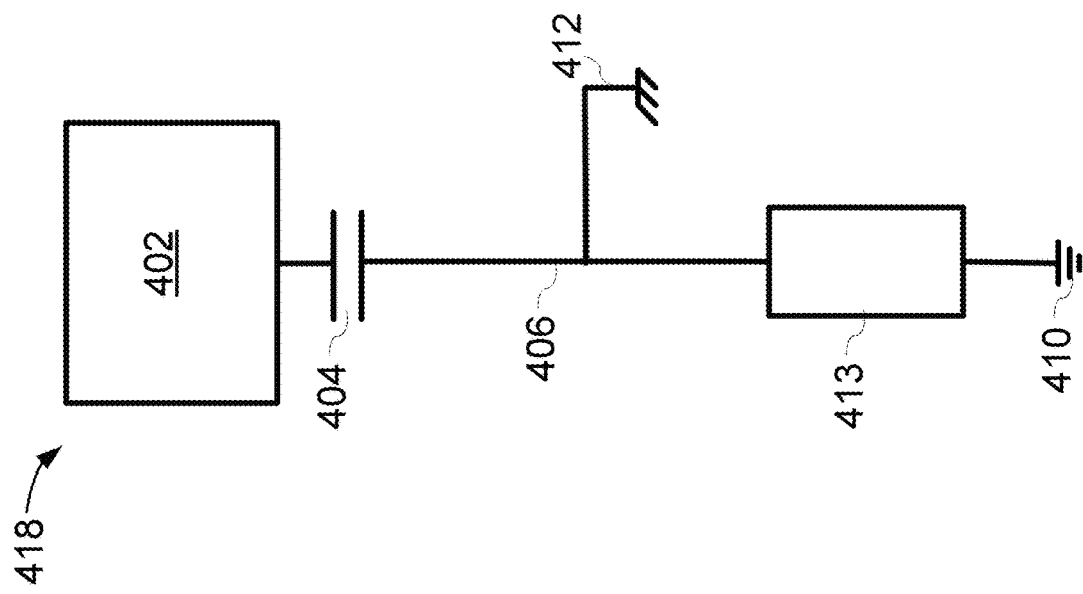
Figure 15B:
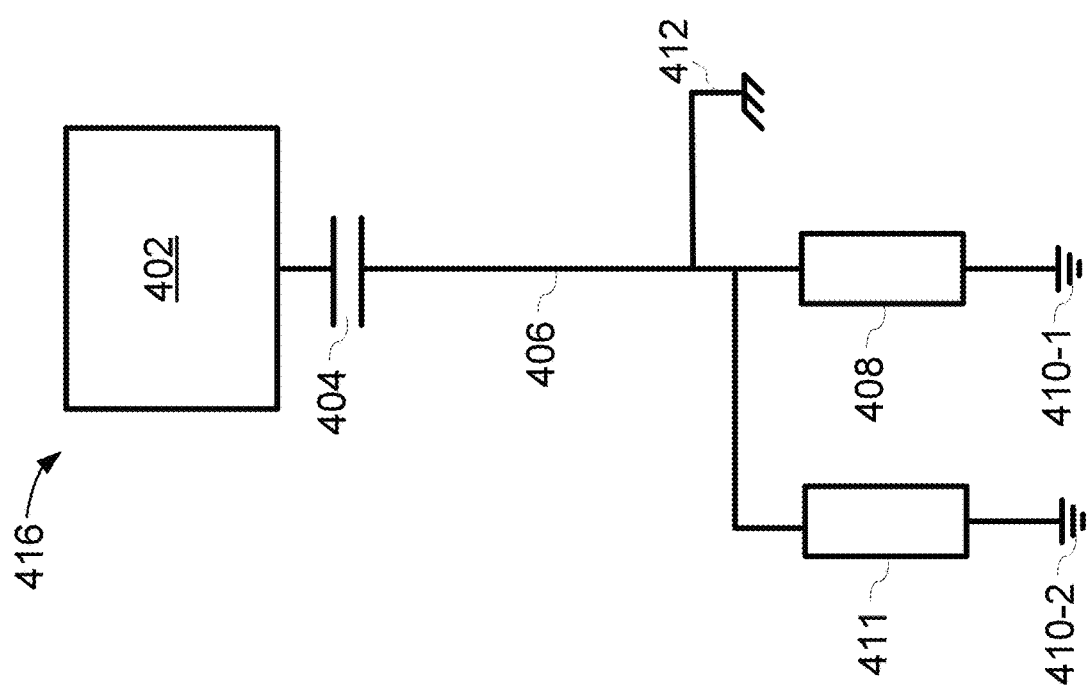

FIGS. 15A-15C illustrate example protective-earth systems, according to some embodiments. FIG. 15A shows a protective-earth system 400 that includes a testing circuit 402 coupled to a protective-earth (PE) line 406 via an isolation capacitor 404. The protective-earth line 406 in FIG. 15A is connected to an enclosure 412 of a medical system and is connected (directly or indirectly) to an electrical ground (GND) line 410. In some embodiments, the protective-earth line 406 is connected to the enclosure 412 via one or more mechanical fasteners (e.g., a screw, nail, or staple). In some embodiments, the protective-earth line 406 is connected to the electrical ground line 410 via one or more mechanical fasteners (e.g., a screw, nail, or staple). FIG. 15A further shows a load 408 representing an impedance of the PE-GND connection as measured by the testing circuit 402.

FIG. 15B shows a protective-earth system 416 that is similar to the protective-earth system 400 in FIG. 15A except that the protective-earth line 406 is connected to two electrical ground lines 410-1 and 410-2 with corresponding loads 408 and 411. In accordance with some embodiments, the protective-earth system 416 represents a scenario where the protective-earth system 400 has an additional electrical connection to the GND line 410 (in addition to a first electrical connection to the GND line represented by the load 408). The additional electrical connection can represent an unintentional short between the PE line 406 and the GND line 410. The unintentional short can be undesirable as it can introduce additional noise into the GND line 410 and/or reduce shielding effects provided by the enclosure 412 to internal components of the medical system. The loads 408 and 411 in FIG. 15B are connected in parallel and thus a total impedance measured by the testing circuit 402 in the protective-earth system 416 is lower as compared to a total impedance (measured by the testing circuit 402 in the protective-earth system 400 (e.g., the load 408 alone).

FIG. 15C shows a protective-earth system 418 that is similar to the protective-earth system 400 in FIG. 15A except that the load 408 in FIG. 15A is replaced with a load 413. In accordance with some embodiments, the load 413 is larger than the load 408 (e.g., represents a larger impedance of the PE-GND connection as measured by the testing circuit 402). In accordance with some embodiments, the protective-earth system 418 represents a scenario where the protective-earth line 406 has higher impedance (as compared to FIG. 15A) due to a degradation of the PE line 406 and/or the connection between the PE line 406 and the GND line 410. The increased impedance can be undesirable as it can increase the likelihood of an electric shock being received by a patient or operator of the medical system.

Figure 16:
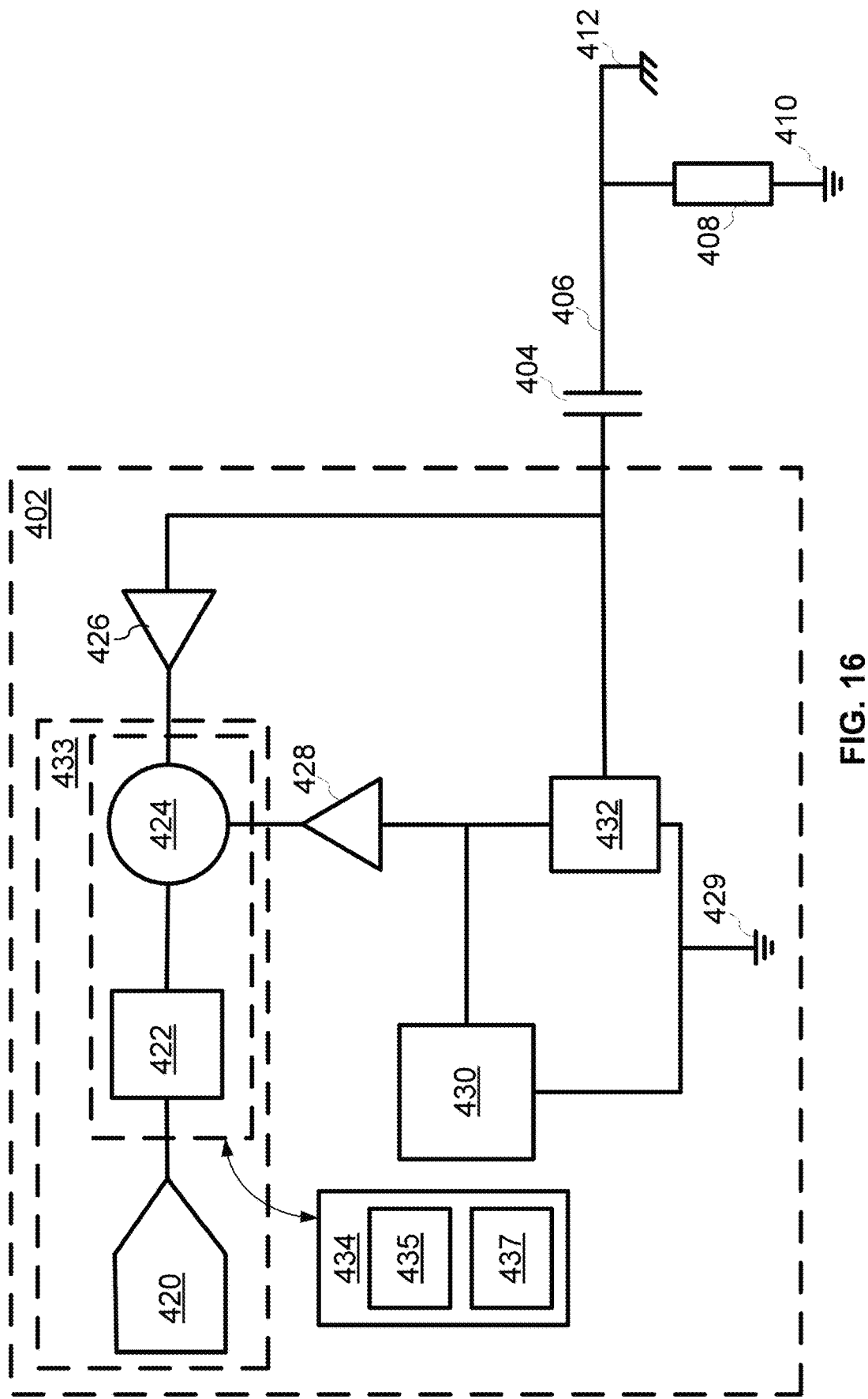
FIG. 16 illustrates an example testing circuit for a protective-earth system, according to some embodiments.

FIG. 16 illustrates components of the testing circuit 402 for a protective-earth system, according to some embodiments. The testing circuit 402 in FIG. 16 includes a signal generator 430 coupled (e.g., connected directly or indirectly) to the isolation capacitor 404 via a voltage-to-current converter (VCC) 432. In some embodiments, the signal generator 430 is also coupled (e.g., connected directly or indirectly) to an electrical ground 429. As shown in FIG. 16, the signal generator 430 is coupled (e.g., connected directly or indirectly) to a lock-in amplifier component 433. In some embodiments, the signal generator 430 is coupled (e.g., connected directly or indirectly) to the lock-in amplifier component 433 via a buffer 428. Also as shown in FIG. 16, the isolation capacitor 404 is coupled (e.g., connected directly or indirectly) to the lock-in amplifier component 433. In some embodiments, the isolation capacitor 404 is coupled (e.g., connected directly or indirectly) to the lock-in amplifier component 433 via a buffer 426. In accordance with some embodiments, the lock-in amplifier component 433 includes an analog mixer 424, a low-pass filter 422, and an analog-to-digital converter (ADC) 420. In this way, no direct current (DC) path is created between the testing circuit 402 and the PE line 406.

In some embodiments, the signal generator 430 is configured to produce a voltage waveform with a carrier frequency ($f_c$). In some embodiments, the carrier frequency is in the range of 20 kilohertz to 500 kilohertz. In some embodiments, the carrier frequency is in the range of 500 kilohertz to 50 megahertz. In some situations, higher frequencies in the range correspond to faster circuit requirements to multiply, filter, and measure the response signal. In some situations, lower frequencies in the range correspond to slower circuit requirements to multiply, filter, and measure the response signal. In some embodiments, the isolation capacitor (e.g., isolation capacitor 404) is sized (e.g., has a capacitance value) so as to function as a high pass filter. In some embodiments, the isolation capacitor is selected to have a capacitance such that a corresponding RC cutoff frequency (e.g., an RC cutoff frequency of the testing circuit) is on the order of the carrier frequency. In some embodiments, the isolation capacitor is selected to have a capacitance such that a corresponding RC cutoff frequency is lower than the carrier frequency (e.g., half of the carrier frequency or an order of magnitude below the carrier frequency). In some embodiments, the signal generator 430 is configured to produce a square or sinusoidal voltage waveform. In some situations, a square waveform may be easier to generate, but more difficult to lock-on (as compared to a sinusoidal waveform) as it includes a range of frequencies.

In some embodiments, the voltage-to-current converter 432 is, or includes, a voltage controlled current source (VCCS). In some embodiments, the analog mixer 424 is an analog multiplier (e.g., an analog multiplying mixer). In some embodiments, the analog mixer 424 is configured to multiply a signal from the PE line 406 (e.g., received via the isolation capacitor 404 and the buffer 426) with the carrier frequency (fc) from the signal generator (e.g., received via the buffer 428). In some embodiments, the signal from the PE line 406 corresponds to (or indicates or is dependent on) the impedance of the load 408. In some embodiments, the low-pass filter 422 is configured to filter out alternating current (AC) frequencies (e.g., to isolate the DC signal). In some embodiments, the low-pass filter 422 is configured to filter out all frequencies, including the carrier frequency, to isolate the DC signal. In some embodiments, the lock-in amplifier component 433 includes a digital lock-in amplifier 434 (e.g., using a discrete fast Fourier transform (DFFT)). For example, the lock-in amplifier component 433 includes an ADC 435 and a digital signal processing (DSP) component 437 configured to perform the lock-in amplification. In some embodiments, the lock-in amplifier component 433 includes the digital lock-in amplifier 434 without (e.g., in place of) the low-pass filter 422 and the analog mixer 424.

In some embodiments, the signal generator 430 is configured to output waveforms with a maximum voltage of less than 1 millivolt (e.g., 100 microvolts, 50 microvolts, or 20 microvolts). In some embodiments, the signal generator 430 is configured to output waveforms with a maximum voltage of at least 1 volt (e.g., 1.8 volts, 2.5 volts, 3.3 volts, or 5 volts). In some embodiments, voltage-to-current converter 432 is configured to output a maximum peak current below a safety threshold (e.g., below 100 microamps, 50 microamps, or 20 microamps).

Figure 17A:
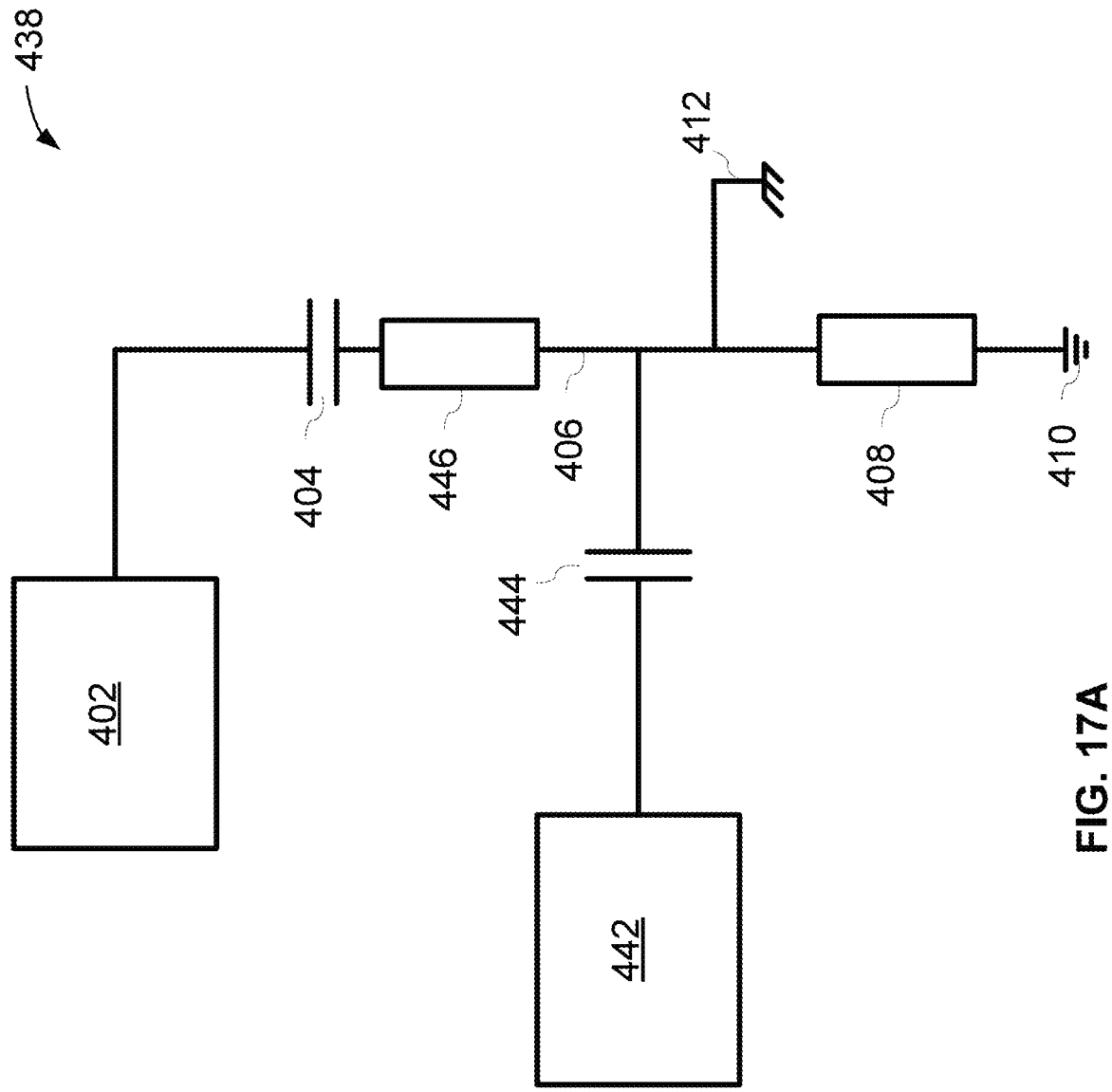
FIGS. 17A and 17B illustrate additional example protective-earth systems, according to some embodiments.

FIG. 17A illustrates a protective-earth system 438 according to some embodiments. The protective-earth system 438 is similar to the protective-earth system 400 except that the protective-earth system 438 includes a second testing circuit 442 connected to the protective earth line 406 via a second isolation capacitor 444. In some embodiments, the second testing circuit 442 is similar to the testing circuit 402 described herein. The protective-earth system 438 is capable of measuring the load or impedance of the PE line 406 when the load or impedance of the PE line 406 is better represented as a distributed load or impedance (e.g., the load or impedance of the PE line 406 is represented by a combination of the load 408 and the load 446, for example due to its length or involvement of one or more joints). In some embodiments, a comparison of the impedance measured by the testing circuit 402 and the impedance measured by the second testing circuit 442 identifies a portion of the PE line 406 that has a changed impedance.

Figure 17B:
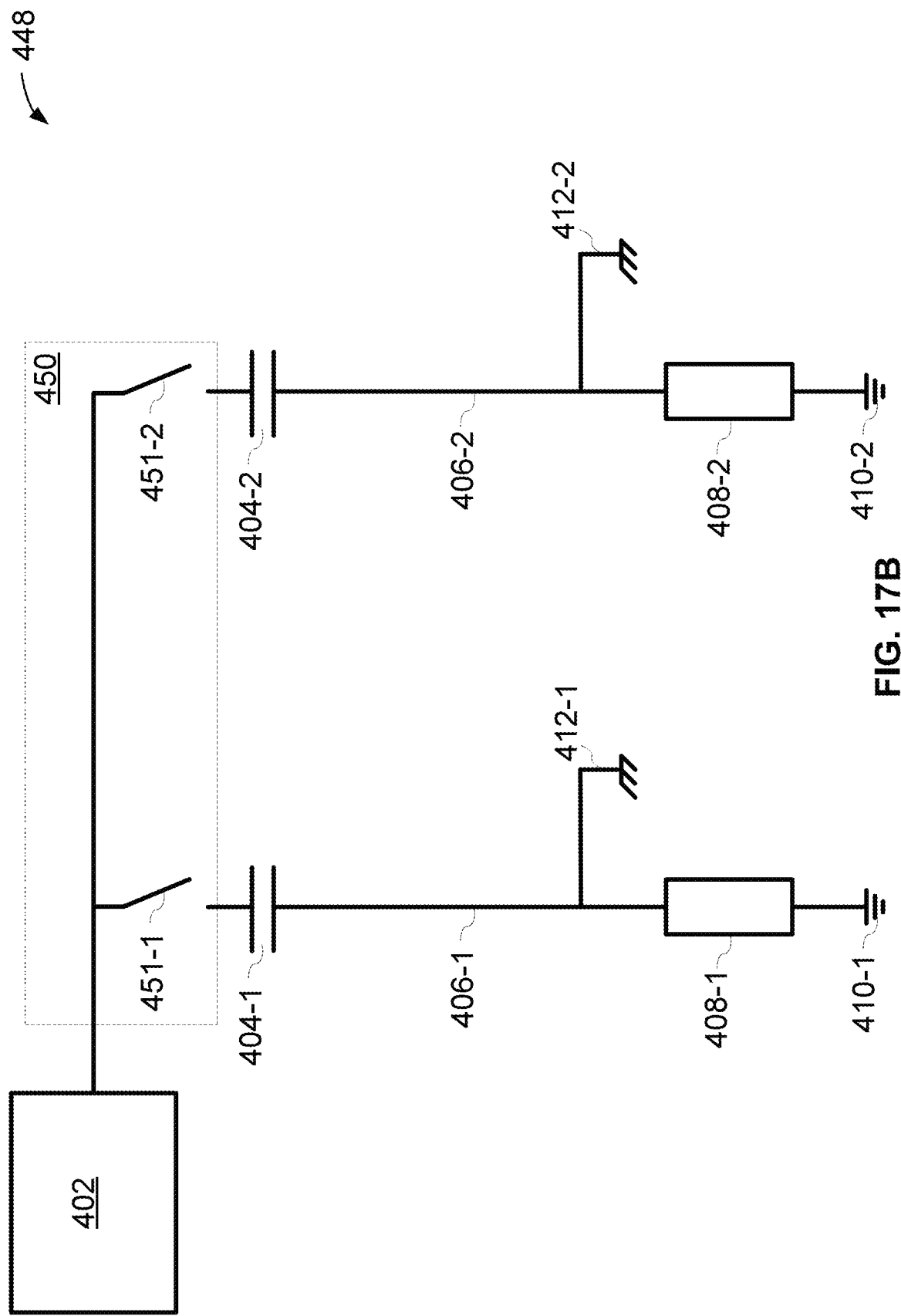

FIG. 17B illustrates a protective-earth system 448 according to some embodiments. The protective-earth system 448 includes a testing circuit 402 coupled to PE lines 406-1 and 406-2 via a switching component 450. In accordance with some embodiments, the switching component 450 includes a switch 451-1 coupled to the PE line 406-1 and a switch 451-2 coupled to the PE line 406-2. The testing circuit 402 is coupled to the PE line 406-1 via the switch 451-1 and the isolation capacitor 404-1. The PE line 406-1 is coupled to an enclosure 412-1 and an electrical ground 410-1 and has a corresponding load 408-1. The testing circuit 402 is coupled to the PE line 406-2 via the switch 451-2 and the isolation capacitor 404-2. The PE line 406-2 is coupled to an enclosure 412-2 and an electrical ground 410-2 and has a corresponding load 408-2.

In some embodiments, the switch component 450 is configured to selectively couple the testing circuit 402 to the PE lines 406-1 and 406-2 so that an impedance of each PE line can be measured. For example, at a first time the switch 451-1 is closed and the switch 451-2 is open. Thus, the testing circuit 402 can measure an impedance of the load 408-1 at the first time. In this example, at a second time the switch 451-1 is open and the switch 451-2 is closed. Thus, the testing circuit 402 can measure an impedance of the load 408-2 at the second time. In this way, the testing circuit 402 is able to monitor and test multiple PE lines 406. In some embodiments, the switch component 450 includes three or more switches (e.g., four or more switches, five or more switches, etc.) for testing three or more PE lines independently.

Figure 18:
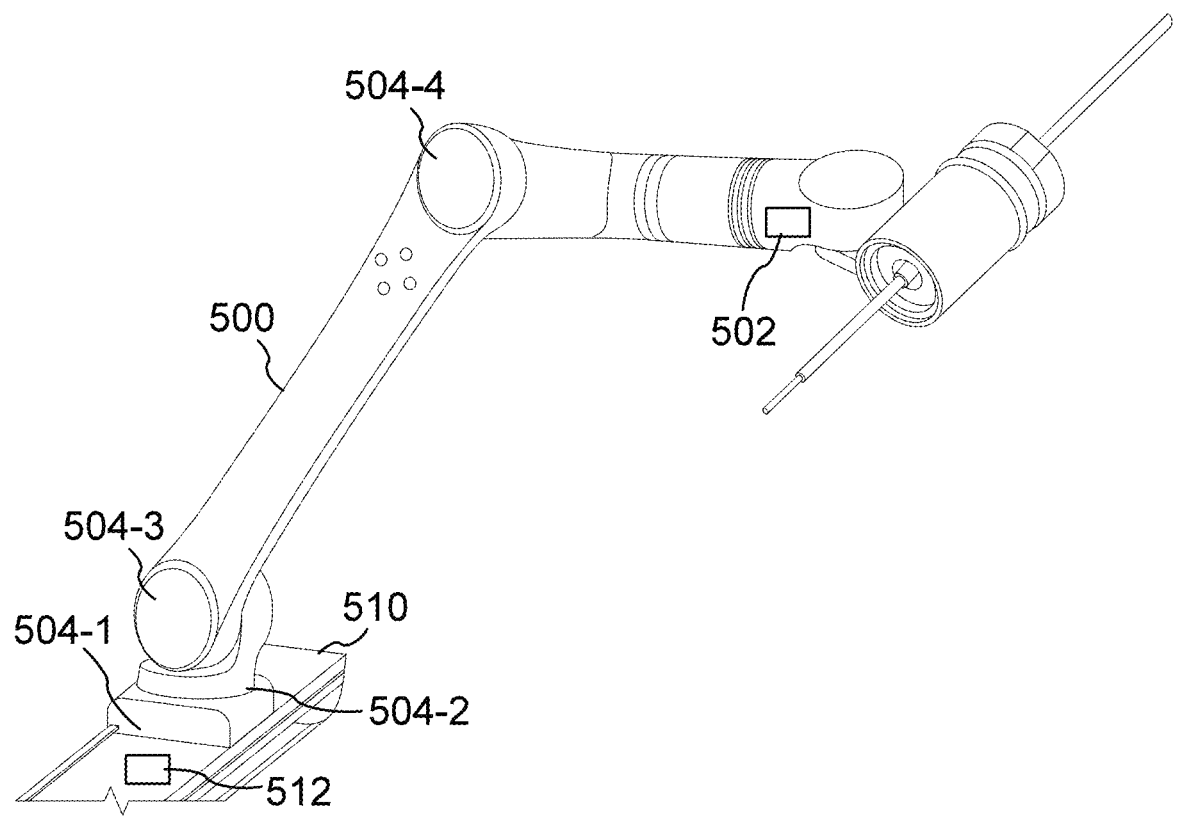
FIG. 18 illustrates an example robotic arm with a protective-earth system, according to some embodiments.

FIG. 18 illustrates a robotic arm 500 with a protective-earth system, according to some embodiments. In some embodiments, the robotic arm 500 is an instance of any one of the robotic arms described previously (e.g., robotic arm 12, 39, 50, 142, 176, 182, or 258). The robotic arm 500 includes a testing circuit 502, joints 504 (e.g., 504-1 through 504-4), an arm support 510, and a protective-earth connection 512 to an electrical ground. Each of the joints 504 includes one or more degrees of freedom (DoFs). In some embodiments, the joint 504-1 is a base joint (A0 joint) located at or near a base of the robotic arm 500. In some embodiments, the joint 504-1 is a prismatic joint that allows the robotic arm 500 to translate (e.g., along the y-axis) along a support 510 (e.g., a fixed frame or an adjustable arm support). In some embodiments, the joint 504-2 rotates with respect to the base joint 504-1. In some embodiments, the joint 504-3 includes multiple DoFs and facilitates both tilt and rotation of the robotic arm with respect to the joint 504-3. In some embodiments, the joint 504-4 comprises an elbow joint. The robotic arm 500 includes a protective-earth line (e.g., one or more conductive enclosures of the robotic arm around multiple links) connecting the testing circuit 502 to the PE connection 512 to the electrical ground in accordance with some embodiments. In some embodiments, the PE line goes through the joints 504 (e.g., the joints 504 may include conductive components for providing connectivity for the PE line). Thus, the PE line can be susceptible to degradation over time due to movement of the joints 504.

In some embodiments, the testing circuit 502 is an instance of the testing circuit 402. The testing circuit 402 is configured to measure an impedance of the PE line and PE connection 512 to the electrical ground in accordance with some embodiments. Thus, the testing circuit 402 is configured to measure any additional impedance introduced via degradation of the PE line at one or more of the joints 504.

Figure 19:
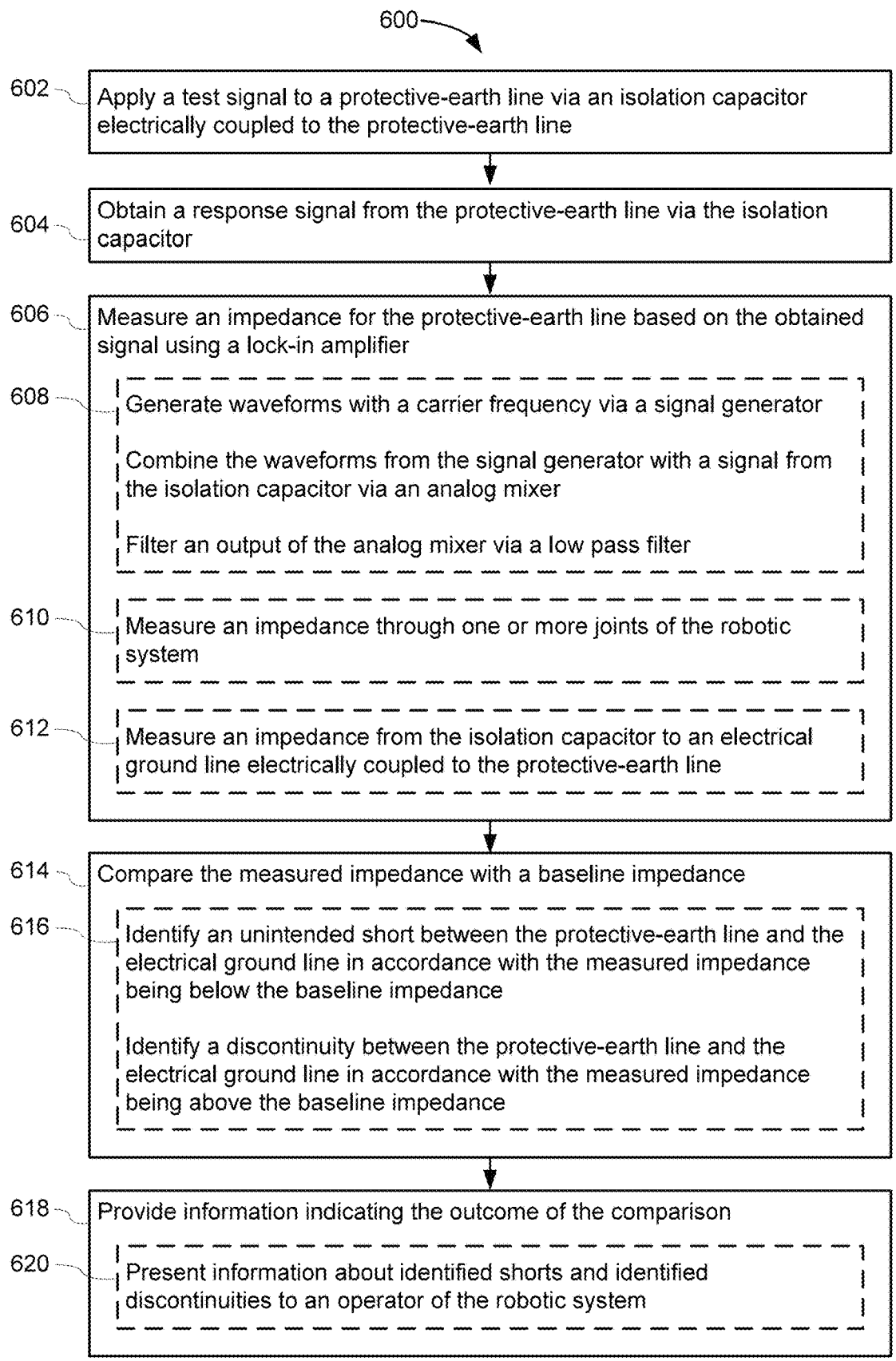
FIG. 19 is a flowchart illustrating an example method for testing a protective-earth line of a robotic system in accordance with some embodiments.

FIG. 19 is a flowchart illustrating a method 600 for testing a protective-earth line of a robotic system in accordance with some embodiments. The method 600 is performed at a robotic system (e.g., the medical system 36) having one or more processors (e.g., the processor(s) 280) and memory (e.g., the memory 282). In some embodiments, the memory (e.g., the memory 282) stores instructions for execution by the one or more processor (e.g., the processor(s) 280). In some embodiments, the robotic system includes a robotic arm. In some embodiments, the robotic arm is coupled to a medical instrument.

The robotic system applies (602) a test signal to a protective-earth line (e.g., the protective-earth line 406) via an isolation capacitor (e.g., the capacitor 404) electrically coupled to the protective-earth line. For example, the testing circuit 402 can apply a test signal to the protective-earth line 406 via the isolation capacitor 404. In some embodiments, the test signal is a sinusoidal or square waveform having a particular frequency (e.g., a carrier frequency). In some embodiments, the test signal is a test current (e.g., the test signal is a current input). In some embodiments, the test signal has a maximum current below a safety threshold for the robotic system (e.g., less than 50 microamps).

The robotic system obtains (604) a response signal from the protective-earth line via the isolation capacitor (e.g., the capacitor 404). In some embodiments, the robotic system receives a voltage signal that corresponds to a test current applied through an impedance load (e.g., the load 408) corresponding to the protective-earth line. In some embodiments, the response signal is a voltage signal having a maximum voltage of less than 100 microvolts (e.g., less than 50 microvolts).

The robotic system measures (606) an impedance for the protective-earth line based on the obtained signal using a lock-in amplifier (e.g., the lock-in amplifier component 433). For example, the robotic system generates a test signal having a carrier frequency and the robotic system uses the lock-in amplifier to isolate and amplify the carrier frequency in the signal received from the protective-earth line in response to the test signal. In some embodiments, the robotic system measures phase data of the obtained signal and correlates the phase data with capacitive and inductive components of the impedance. In some embodiments, the robotic system uses the capacitive and inductive components of the impedance to determine an effectiveness of the protective-earth connection to the electrical ground.

In some embodiments, the robotic system: (i) generates (608) waveforms with a carrier frequency via a signal generator (e.g., the signal generator 430); (ii) combines the waveforms from the signal generator with a signal through the isolation capacitor via an analog multiplying mixer (e.g., the analog mixer 424); and (iii) filters an output of the analog mixer via a low-pass filter (e.g., the low-pass filter 422). For example, the robotic system uses the analog mixer 424 (e.g., an analog multiplier) to multiply a carrier frequency from the signal generator 430 with a current-induced voltage at the isolation capacitor 404. In this example, the output of the analog mixer is filtered through the low-pass filter 422 to isolate the DC signal and passed to the ADC 420 for measurement. In some embodiments, the output of the low-pass filter is a direct current (DC) signal. In some cases, the direct current signal is proportional to an impedance of the protective-earth line and connection to the electrical ground (e.g., the load 408).

In some embodiments, the robotic system measures (610) an impedance through one or more joints of the robotic system (e.g., the joints 504). In some embodiments, the one or more joints are configured to allow free infinite rotation. Accordingly, in some embodiments, the PE line is passed through the one or more joints via a slip-ring and brushes interface.

In some embodiments, the robotic system measures (612) an impedance through the isolation capacitor to an electrical ground line (e.g., the electrical ground line 410) electrically coupled to the protective-earth line. In some embodiments, measuring an impedance for the protective-earth line includes determining an impedance between the protective-earth line and an electrical ground.

The robotic system compares (614) the measured impedance with a baseline impedance. In some embodiments, the baseline impedance is 10 ohms or less (e.g., 10 ohms, 5 ohms, 2 ohms, or 1 ohm). In some embodiments, the baseline impedance is an impedance due to expected parasitics of the robotic system (e.g., wires series resistance, connectors, copper traces, and the like). For example, in some cases, the baseline impedance corresponds to an impedance of the protective-earth line measured at production (e.g., prior to sale or deployment of the robotic system). In some embodiments, the baseline impedance is measured during production or prior to sale or deployment of the robotic system. In some embodiments, the baseline impedance is measured during maintenance operations (e.g., in regular maintenance).

In some embodiments, the robotic system identifies (616) an unintended short between the protective-earth line and the electrical ground line (e.g., an additional unintended short due to fault) in accordance with the measured impedance being below the baseline impedance. In some embodiments, the robotic system identifies a discontinuity between the protective-earth line and the electrical ground line in accordance with the measured impedance being above the baseline impedance.

The robotic system provides (618) information indicating the outcome of the comparison. For example, the robotic system provides the information to an operator of the robotic system. In some embodiments, the robotic system provides the information on a display of the robotic system (e.g., the touchscreen 26). In some embodiments, the robotic system provides the information to a device communicatively coupled to the robotic system (e.g., a computer system or an alarm on a same network as the robotic system). In some embodiments, providing the information includes initiating an alert or warning that the robotic system is unsafe for use (e.g., due to discontinuity of the PE line). In some configurations, the alert or warning includes a visible alert or warning (e.g., a warning indicator). In some configurations, the alert or warning includes an audible alert or warning (e.g., a warning sound).

In some embodiments, the robotic system presents (620) information about identified shorts and identified discontinuities to an operator of the robotic system. In some embodiments, the robotic system presents the measured impedance value and information regarding whether the measured impedance value is above or below an expected impedance value. In some embodiments, the measured impedance value and the information regarding whether the measured impedance value is above or below an expected impedance value are presented on a display device (e.g., a monitor or a screen of the console 31).

In some embodiments, the robotic system includes: (i) an electrical ground line (e.g., the electric ground line 410); (ii) a protective-earth line (e.g., the protective-earth line 406) electrically coupled to the electrical ground line at a first point; and (iii) a testing circuit (e.g., the testing circuit 402) coupled to the protective-earth line at a second point via an isolation capacitor (e.g., the isolation capacitor 404).

In some embodiments, the testing circuit includes a lock-in amplifier (e.g., the lock-in amplifier component 433) and is configured to measure an impedance for the protective-earth line. In some embodiments, the protective-earth line is shorted to the electrical ground line at the first point. In some embodiments, the testing circuit is not directly coupled to the protective-earth line (e.g., only coupled via the isolation capacitor). In some embodiments, the capacitor coupled with the protective-earth line forms a high pass filter. In some embodiments, the capacitor is sized in accordance with a carrier frequency of the testing circuit. In some embodiments, the impedance for the protective-earth line includes the impedance of the isolation capacitor, the impedance of the protective-earth line, and the impedance of the electrical coupling between the protective-earth line and the electrical ground line.

In some embodiments, the lock-in amplifier includes: (i) a signal generator (e.g., the signal generator 430) coupled to the isolation capacitor and configured to generate waveforms with a carrier frequency; (ii) an analog mixer (e.g., the analog mixer 424) for combining the waveforms from the signal generator with a signal through the isolation capacitor; and (iii) a low-pass filter (e.g., the low-pass filter 422) coupled to an output of the analog mixer.

In some embodiments, the low-pass filter is configured to isolate the DC signal (e.g., filter out all AC frequencies). In some embodiments, an ADC (e.g., the ADC 420) is coupled to the output of the low-pass filter. In some embodiments, the signal generator is configured to generate a sinusoidal signal or a square signal. In some embodiments, the signal generator includes a voltage waveform generator coupled to a voltage-to-current converter (VCC) or a voltage-controlled current source (VCCS). In some embodiments, the analog mixer is, or includes, an analog multiplier.

In some embodiments, the signal generator is configured to output signals with a maximum peak current below a safety threshold (e.g., a safety threshold of 50 microamps).

In some embodiments, the lock-in amplifier includes a digital signal processing (DSP) circuit (e.g., the DSP circuit 437 of the digital lock-in amplifier 434). For example, the lock-in amplifier includes an ADC 435 and a DSP circuit 437 coupled to the output of the ADC. In some embodiments, the DSP circuit 437 is configured to perform lock-in amplification via a DFFT operation.

In some embodiments, the second point is remote from the first point, and the testing circuit is configured to measure an impedance between the first point and the second point. For example, the protective-earth line is connected to the electrical ground line at a base of the robotic system and the testing circuit is coupled to the protective-earth line at a top of the robotic system. In this example, the testing circuit is configured to measure an impedance from the top of the robotic system to the base of the robotic system. As another example, FIG. 18 shows the testing circuit 502 at one end of the robotic arm 500 (e.g., at a distal end of a robotic arm) and the PE connection 512 to electrical ground at an opposite end of the robotic arm 500 (e.g., at a proximal end of the robotic arm).

In some embodiments, the robotic system includes one or more joints and measuring the impedance between the first point and the second point includes measuring an impedance through the one or more joints. For example, the testing circuit 502 in FIG. 18 measures an impedance through the joints 504 as part of measuring an impedance of the PE line to electrical ground.

In some embodiments, (i) the testing circuit is a first testing circuit; (ii) the robotic system further includes a second testing circuit coupled to the protective-earth line at a third point; and (iii) the second testing circuit is configured to measure an impedance between the first point and the third point (e.g., FIG. 17A). For example, the first testing circuit is located in a first robotic arm of the robotic system and the second testing circuit is located in a second robotic arm of the robotic system. In this example, each testing circuit measures an impedance of the protective-earth line for the corresponding robotic arm. In some embodiments, the first testing circuit uses a first carrier frequency and the second testing circuit uses a second carrier frequency, different from the first carrier frequency (e.g., 1%, 5%, or 10% different). In some embodiments, the first testing circuit and the second testing circuit use a same carrier frequency.

In some embodiments, (i) the robotic system further includes a second protective-earth line (e.g., the protective-earth line 406-2) electrically coupled to the electrical ground line (e.g., the electrical ground 410-2) at a third point; and (ii) the testing circuit is configured to: (a) measure a first impedance between the second point and the first point; and (b) measure a second impedance between the second point and the third point. For example, the protective-earth system 448 in FIG. 17B shows the testing circuit 402 electrically coupled to the protective-earth lines 406-1 and 406-2 and configured to measure impedances of the protective-earth lines.

In some embodiments, (i) the isolation capacitor is a first isolation capacitor; (ii) the testing circuit is coupled to the second protective-earth line (e.g., the protective-earth line 406-2) via a second isolation capacitor (e.g., the isolation capacitor 404-2); and (iii) the testing circuit further includes a switching component (e.g., the switching component 450) for selectively coupling the lock-in amplifier to the first isolation capacitor or the second isolation capacitor.

In some embodiments, the robotic system further includes a controller (e.g., the processor(s) 280) coupled to the testing circuit, and the controller is configured to: (i) compare the impedance for the protective-earth line to a baseline impedance value; (ii) identify a (unintended) short between the protective-earth line and the electrical ground line in accordance with the impedance for the protective-earth line being below the baseline impedance value; and (iii) identify a discontinuity between the protective-earth line and the electrical ground line in accordance with the impedance for the protective-earth line being above the baseline impedance value. In some embodiments, the controller includes a hardware comparator circuit. In some embodiments, identification of a discontinuity causes the robotic system to automatically enter an emergency-stop state.

In some embodiments, the robotic system further includes a user interface (e.g., the console 31) configured to present information about identified shorts and identified discontinuities to an operator of the robotic system. For example, the user interface includes is a display panel, a warning light, and/or a speaker to emit an audible warning.

In some embodiments, the robotic system is configured to periodically test the protective-earth line using the testing circuit (e.g., weekly, daily, hourly, etc.). In some embodiments, the robotic system is configured to test the protective-earth line using the testing circuit as part of a start-up (power-on) sequence for the robotic system. In some embodiments, the robotic system is configured to test the protective-earth line prior to use in a medical operation. In some embodiments, the robotic system is configured to test the protective-earth line prior to a procedure that requires a high voltage operation (e.g., electrocauterization). In some embodiments, the robotic system is configured to continuously test the protective-earth line using the testing circuit.

In some embodiments, the robotic system further includes a metal enclosure (e.g., the enclosure 412), and the protective-earth line is electrically coupled to the metal enclosure. In some embodiments, the robotic system includes a housing, and the testing circuit is arranged within the housing. In some embodiments, the housing is the enclosure 412. In some embodiments, the robotic system includes an electrically conductive enclosure. In some embodiments, the protective-earth line is integrated with the metal enclosure. In some embodiments, the metal enclosure constitutes the protective-earth line.

In some embodiments, the robotic system includes: (i) an electrical ground line; (ii) a protective-earth line; and (iii) a testing circuit coupled to the protective-earth line via an isolation capacitor electrically coupled to the protective-earth line. In some embodiments, the testing circuit is configured to measure an impedance through the isolation capacitor to the electrical ground line via the protective-earth line. In some embodiments, the testing circuit includes a lock-in amplifier.

3. Implementing Systems and Terminology.

Figure 20:
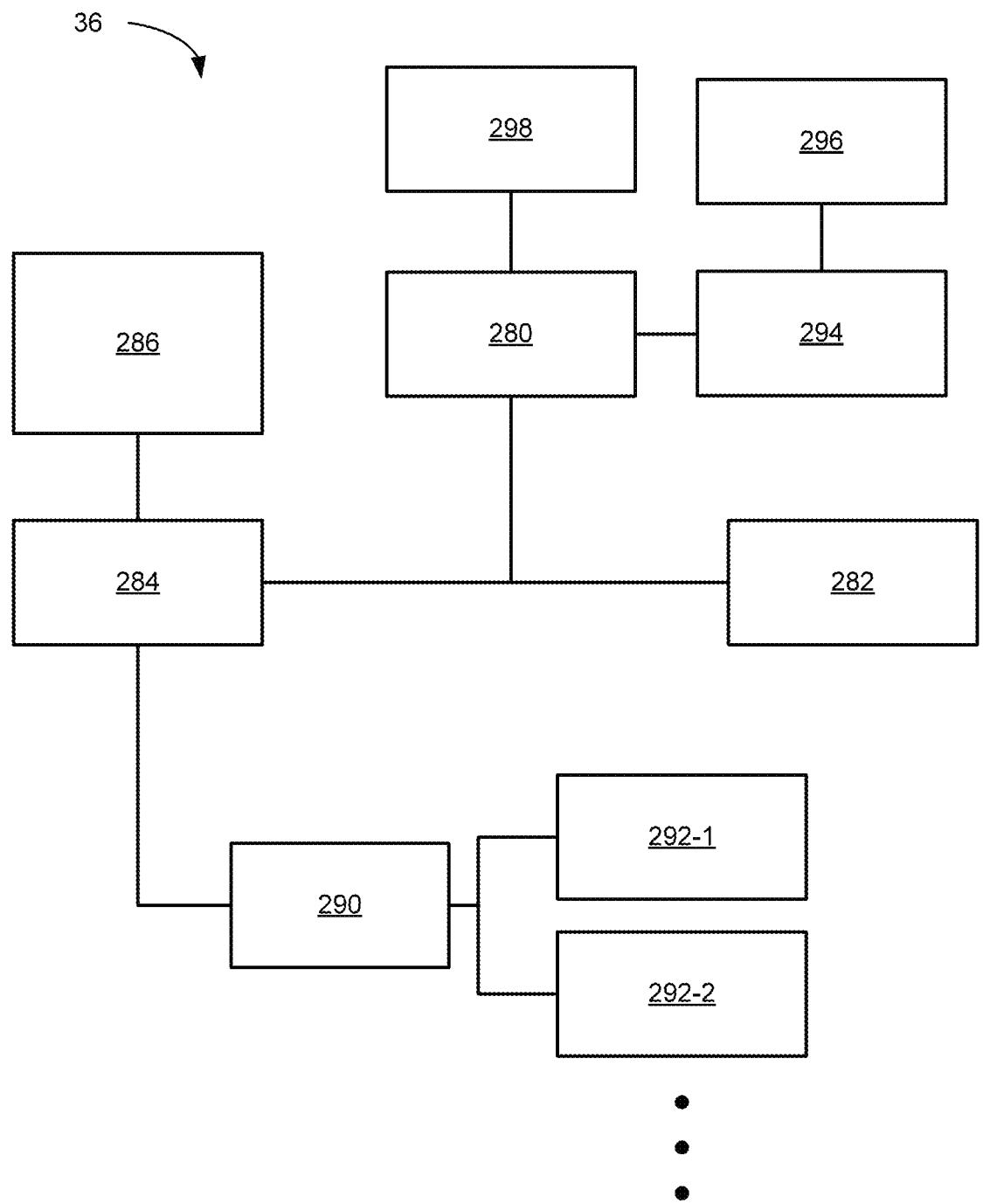
FIG. 20 is a schematic diagram illustrating electronic components of a medical system in accordance with some embodiments.

FIG. 20 is a schematic diagram illustrating electronic components of a system (e.g., a medical and/or robotic system). The system includes one or more processors 280, which are in communication with a computer-readable storage medium of memory 282 (e.g., computer memory devices, such as random-access memory, read-only memory, static random-access memory, and non-volatile memory, and other storage devices, such as a hard drive, an optical disk, a magnetic tape recording, or any combination thereof) storing instructions for performing any methods described herein (e.g., operations described with respect to FIG. 19). The one or more processors 280 are in communication with a testing circuit 294 and a user interface 298. In some embodiments, the user interface 298 includes one or more a human-machine interface (HMI) components, such as a console (e.g., the console 31), a display (e.g., the touchscreen 26), a speaker, and/or a warning light (e.g., an LED). In some embodiments, the testing circuit 294 is an instance of the testing circuit 402. The testing circuit 294 is in communication with (or electrically coupled to) a protective-earth line 296. In some embodiments, the protective-earth line 296 is an instance of the protective-earth line 406. In some embodiments, the protective-earth line 296 is integrated with, or coupled to, an enclosure of the system (e.g., a metal housing for the system). The testing circuit 294 is configured to test the protective-earth line 296 (e.g., send test signals to, and receive response signals from, the protective-earth line 296). In some embodiments, the testing circuit 294 is configured to send the results of the test to the processor(s) 280. In some embodiments, the testing circuit 294 is configured to send data obtained for the test (e.g., intermediate data) to the processor(s) 280 for further processing and analysis. For example, the testing circuit 294 measures an impedance for the protective-earth line 296 and sends the measured impedance to the processor(s) 280 to be compared with a baseline impedance (e.g., a baseline impedance stored in the memory 282). In some embodiments, the one or more processors 280 are configured to analyze the test data from the testing circuit 294 and generate test information to be provided to a user of the system (e.g., provided via the user interface 298).

The one or more processors 280 are also in communication with an input/output controller 284 (via a system bus or any suitable electrical circuit). The input/output controller 284 receives user input from the input device 286 (e.g., the robotic arm 182, or the instrument 200) and, optionally, sensor data from one or more sensors, and relays the data and user input to the one or more processors 280. The input/output controller 284 also receives instructions and/or data from the one or more processors 280 and relays the instructions and/or data to one or more actuators, such as motors 292-1 and 292-2 (e.g., actuators and motors for driving robotic arms of the system). In some embodiments, the input/output controller 284 is coupled to one or more actuator controllers 290 and provides instructions and/or data to at least a subset of the one or more actuator controllers 290, which, in turn, provide control signals to selected actuators 292. In some embodiments, the one or more actuator controllers 290 are integrated with the input/output controller 284 and the input/output controller 284 provides control signals directly to the one or more actuators 292 (e.g., without a separate actuator controller).

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

4. Illustration of Subject Technology as Clauses.

Some embodiments or implementations are described with respect to the following clauses:

Clause 1. A robotic system comprising:
an electrical ground line;
a protective-earth line electrically coupled to the electrical ground line at a first point; and
a testing circuit coupled to the protective-earth line at a second point via an isolation capacitor,
the testing circuit comprising a lock-in amplifier and configured to measure an impedance for the protective-earth line.

Clause 2. The robotic system of Clause 1, wherein the lock-in amplifier comprises:
a signal generator coupled to the isolation capacitor and configured to generate waveforms with a carrier frequency;
an analog mixer for combining the waveforms from the signal generator with a signal from the isolation capacitor; and
a low-pass filter coupled to an output of the analog mixer.

Clause 3. The robotic system of Clause 2, wherein the signal generator is configured to output signals with a maximum peak current below a safety threshold.

Clause 4. The robotic system of any of Clauses 1-3, wherein the lock-in amplifier comprises a digital signal processing (DSP) circuit.

Clause 5. The robotic system of any of Clauses 1-4, wherein the second point is remote from the first point, and the testing circuit is configured to measure an impedance between the first point and the second point.

Clause 6. The robotic system of Clause 5, wherein the robotic system comprises one or more joints and wherein measuring the impedance between the first point and the second point comprises measuring an impedance through the one or more joints.

Clause 7. The robotic system of Clause 5 or Clause 6, wherein:
the testing circuit is a first testing circuit;
the robotic system further comprises a second testing circuit coupled to the protective-earth line at a third point; and
the second testing circuit is configured to measure an impedance between the first point and the third point.

Clause 8. The robotic system of any of Clauses 1-7, further comprising: a second protective-earth line electrically coupled to the electrical ground line at a third point; and
wherein the testing circuit is configured to:
measure a first impedance between the second point and the first point; and
measure a second impedance between the second point and the third point.

Clause 9. The robotic system of Clause 8, wherein:
the isolation capacitor is a first isolation capacitor;
the testing circuit is coupled to the second protective-earth line via a second isolation capacitor; and
the testing circuit further comprises a switching component for selectively coupling the lock-in amplifier to the first isolation capacitor or the second isolation capacitor.

Clause 10. The robotic system of any of Clauses 1-9, further comprising a controller coupled to the testing circuit, wherein the controller is configured to:
compare the impedance for the protective-earth line to a baseline impedance value;
identify a short between the protective-earth line and the electrical ground line in accordance with the impedance for the protective-earth line being below the baseline impedance value; and identify a discontinuity between the protective-earth line and the electrical ground line in accordance with the impedance for the protective-earth line being above the baseline impedance value.

Clause 11. The robotic system of Clause 10, further comprising a user interface configured to present information about identified shorts and identified discontinuities to an operator of the robotic system.

Clause 12. The robotic system of any of Clauses 1-11, wherein the robotic system is configured to periodically test the protective-earth line using the testing circuit.

Clause 13. The robotic system of any of Clauses 1-12, wherein the robotic system is configured to test the protective-earth line using the testing circuit as part of a start-up sequence for the robotic system.

Clause 14. The robotic system of any of Clauses 1-13, further comprising a metal enclosure, wherein the protective-earth line is electrically coupled to the metal enclosure.

Clause 15. A method for testing a protective-earth line of a robotic system, the method comprising:
applying a test signal to the protective-earth line via an isolation capacitor electrically coupled to the protective-earth line;
obtaining a signal from the protective-earth line via the isolation capacitor in response to the test signal;
measuring an impedance for the protective-earth line based on the obtained signal, the measuring performed by a lock-in amplifier;
comparing the measured impedance with a baseline impedance; and
providing information indicating the outcome of the comparison.

Clause 16. The method of Clause 15, wherein the measuring comprises: generating waveforms with a carrier frequency via a signal generator;
combining the waveforms from the signal generator with a signal through the isolation capacitor via an analog mixer; and
filtering an output of the analog mixer via a low-pass filter.

Clause 17. The method of Clause 15 or Clause 16, wherein measuring the impedance for the protective-earth line comprises measuring an impedance through one or more joints of the robotic system.

Clause 18. The method of any of Clauses 15-17, wherein measuring the impedance for the protective-earth line comprises measuring an impedance through the isolation capacitor to an electrical ground line electrically coupled to the protective-earth line.

Clause 19. The method of Clause 18, wherein the comparing comprises: identifying a short between the protective-earth line and the electrical ground line in accordance with the measured impedance being below the baseline impedance; and identifying a discontinuity between the protective-earth line and the electrical ground line in accordance with the measured impedance being above the baseline impedance.

Clause 20. The method of Clause 19, wherein providing the information indicating the outcome of the comparison comprises presenting information about identified shorts and identified discontinuities to an operator of the robotic system.

Clause 21. The method of any of Clauses 15-20, wherein the method is performed as part of a start-up sequence for the robotic system.

Clause 22. A robotic system comprising:
an electrical ground line;
a protective-earth line; and
a testing circuit coupled to the protective-earth line via an isolation capacitor electrically coupled to the protective-earth line and configured to measure an impedance through the isolation capacitor to the electrical ground line via the protective-earth line.

Clause 23. The robotic system of Clause 22, wherein the testing circuit includes a lock-in amplifier.

Clause 24. A method for testing a protective-earth line of a robotic system, the method comprising:
providing a test current to the protective-earth line via an isolation capacitor electrically coupled to the protective-earth line;
obtaining a voltage signal through the isolation capacitor in response to the test current;
determining an impedance for the protective-earth line based on the obtained voltage signal; and
providing information indicating continuity of the protective-earth line based on the determined impedance.

Clause 25. The method of Clause 24, wherein the test current is provided at a carrier frequency and the method further includes amplifying a component of the voltage signal having the carrier frequency with a lock-in amplifier.

What is claimed is:

1. A robotic system comprising:
an electrical ground line;
a protective-earth line electrically coupled to the electrical ground line at a first point; and
a testing circuit coupled to the protective-earth line at a second point via an isolation capacitor, the testing circuit comprising a lock-in amplifier and configured to measure an impedance for the protective-earth line.

2. The robotic system of claim 1, wherein the lock-in amplifier comprises:
a signal generator coupled to the isolation capacitor and configured to generate waveforms with a carrier frequency;
an analog mixer for combining the waveforms from the signal generator with a signal from the isolation capacitor; and
a low-pass filter coupled to an output of the analog mixer.

3. The robotic system of claim 2, wherein the signal generator is configured to output signals with a maximum peak current below a safety threshold.

4. The robotic system of claim 1, wherein the lock-in amplifier comprises a digital signal processing (DSP) circuit.

5. The robotic system of claim 1, wherein the second point is remote from the first point, and the testing circuit is configured to measure an impedance between the first point and the second point.

6. The robotic system of claim 5, wherein the robotic system comprises one or more joints and wherein measuring the impedance between the first point and the second point comprises measuring an impedance through the one or more joints.

7. The robotic system of claim 5, wherein:
the testing circuit is a first testing circuit;
the robotic system further comprises a second testing circuit coupled to the protective-earth line at a third point; and
the second testing circuit is configured to measure an impedance between the first point and the third point.

8. The robotic system of claim 1, further comprising:
a second protective-earth line electrically coupled to the electrical ground line at a third point; and
wherein the testing circuit is configured to:
measure a first impedance between the second point and the first point; and
measure a second impedance between the second point and the third point.

9. The robotic system of claim 8, wherein:
the isolation capacitor is a first isolation capacitor;
the testing circuit is coupled to the second protective-earth line via a second isolation capacitor; and
the testing circuit further comprises a switching component for selectively coupling the lock-in amplifier to the first isolation capacitor or the second isolation capacitor.

10. The robotic system of claim 1, further comprising a controller coupled to the testing circuit, wherein the controller is configured to:

compare the impedance for the protective-earth line to a baseline impedance value;

identify a short between the protective-earth line and the electrical ground line in accordance with the impedance for the protective-earth line being below the baseline impedance value; and identify a discontinuity between the protective-earth line and the electrical ground line in accordance with the impedance for the protective-earth line being above the baseline impedance value.

11. The robotic system of claim 10, further comprising a user interface configured to present information about identified shorts and identified discontinuities to an operator of the robotic system.

12. The robotic system of claim 1, wherein the robotic system is configured to periodically test the protective-earth line using the testing circuit.

13. The robotic system of claim 1, wherein the robotic system is configured to test the protective-earth line using the testing circuit as part of a start-up sequence for the robotic system.

14. The robotic system of claim 1, further comprising a metal enclosure, wherein the protective-earth line is electrically coupled to the metal enclosure.

15. A method for testing a protective-earth line of a robotic system, the method comprising:

applying a test signal to the protective-earth line via an isolation capacitor electrically coupled to the protective-earth line;

obtaining a signal from the protective-earth line via the isolation capacitor in response to the test signal;

measuring an impedance for the protective-earth line based on the obtained signal, the measuring performed by a lock-in amplifier;

comparing the measured impedance with a baseline impedance; and providing information indicating the outcome of the comparison.

16. The method of claim 15, wherein the measuring comprises:

generating waveforms with a carrier frequency via a signal generator;

combining the waveforms from the signal generator with a signal through the isolation capacitor via an analog mixer; and filtering an output of the analog mixer via a low-pass filter.

17. The method of claim 15, wherein measuring the impedance for the protective-earth line comprises measuring an impedance through the isolation capacitor to an electrical ground line electrically coupled to the protective-earth line.

18. The method of claim 17, wherein the comparing comprises:

identifying a short between the protective-earth line and the electrical ground line in accordance with the measured impedance being below the baseline impedance; and identifying a discontinuity between the protective-earth line and the electrical ground line in accordance with the measured impedance being above the baseline impedance.

19. A robotic system comprising:

an electrical ground line;

a protective-earth line; and a testing circuit coupled to the protective-earth line via an isolation capacitor electrically coupled to the protective-earth line and configured to measure an impedance through the isolation capacitor to the electrical ground line via the protective-earth line.

20. The robotic system of claim 19, wherein the testing circuit includes a lock-in amplifier.

* * * * *